United States Patent
Eggert et al.

(10) Patent No.: US 11,395,757 B2
(45) Date of Patent: Jul. 26, 2022

(54) CONTINENT OSTOMY VALVE AND METHOD OF USE

(71) Applicants: Mayo Foundation for Medical Education and Research, Rochester, MN (US); Boston Scientific SciMed, Inc., Maple Grove, MN (US)

(72) Inventors: Joel T. Eggert, St. Paul, MN (US); Douglas Pennington, Stillwater, MN (US); James P. Rohl, Prescott, WI (US); William A. Faubion, Rochester, MN (US); Eric J. Dozois, Rochester, MN (US); Jonathan P. P. Fettig, Forest Lake, MN (US); Douglas Dean Pagoria, Forest Lake, MN (US)

(73) Assignees: Boston Scientific Scimed, Inc., Maple Grove, MN (US); Mayo Foundation for Medical Education and Research, Rochester, MN (US)

( * ) Notice: Subject to any disclaimer, the term of this patent is extended or adjusted under 35 U.S.C. 154(b) by 362 days.

(21) Appl. No.: 16/557,634

(22) Filed: Aug. 30, 2019

(65) Prior Publication Data

US 2019/0380860 A1 Dec. 19, 2019

Related U.S. Application Data

(62) Division of application No. 15/079,397, filed on Mar. 24, 2016, now Pat. No. 10,441,455.

(60) Provisional application No. 62/142,206, filed on Apr. 2, 2015.

(51) Int. Cl.
*A61F 5/445* (2006.01)
*A61F 5/44* (2006.01)

(52) U.S. Cl.
CPC ............ *A61F 5/4405* (2013.01); *A61F 5/445* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,344,434 A | * | 8/1982 | Robertson | A61F 5/445 604/338 |
| 4,381,765 A | * | 5/1983 | Burton | A61F 5/445 604/277 |
| 4,634,421 A | * | 1/1987 | Hegemann | A61F 2/0009 604/277 |
| 4,804,375 A | * | 2/1989 | Robertson | A61F 5/4405 604/323 |

(Continued)

FOREIGN PATENT DOCUMENTS

| | | |
|---|---|---|
| EP | 1059902 B1 | 7/2008 |
| EP | 1059902 B1 | 7/2008 |

(Continued)

OTHER PUBLICATIONS

International Search Report for International Application No. PCT/US2016/024034 dated Aug. 24, 2016, 15 pages.

*Primary Examiner* — Guy K Townsend
(74) *Attorney, Agent, or Firm* — Knobbe, Martens, Olson & Bear, LLP

(57) ABSTRACT

Methods and materials related to ostomy devices, and particularly to valves for use with continent ostomies (e.g., ileostomies) are provided herein.

9 Claims, 22 Drawing Sheets

(56) References Cited

U.S. PATENT DOCUMENTS

| | | | | |
|---|---|---|---|---|
| 5,125,916 | A * | 6/1992 | Panebianco | A61F 5/445 604/328 |
| 5,287,852 | A * | 2/1994 | Arkinstall | A61M 16/0465 128/207.14 |
| 5,556,385 | A * | 9/1996 | Andersen | A61J 15/0042 604/174 |
| 5,569,216 | A * | 10/1996 | Kim | A61F 2/0013 604/277 |
| 6,033,390 | A * | 3/2000 | von Dyck | A61F 5/445 604/174 |
| 6,328,720 | B1 * | 12/2001 | McNally | A61J 15/0069 604/335 |
| 6,350,255 | B1 * | 2/2002 | von Dyck | A61F 5/441 604/338 |
| 6,485,476 | B1 * | 11/2002 | von Dyck | A61F 5/441 604/332 |
| 7,001,367 | B2 * | 2/2006 | Arkinstall | A61F 5/445 604/337 |
| 8,388,586 | B2 * | 3/2013 | Weig | A61F 5/445 604/338 |
| 8,449,512 | B2 | 5/2013 | Villani et al. | |
| 8,529,429 | B2 * | 9/2013 | Gobel | A61M 25/1002 600/32 |
| 8,821,464 | B2 * | 9/2014 | Hanuka | A61F 5/441 604/333 |
| 8,998,862 | B2 * | 4/2015 | Hanuka | A61F 5/4405 604/318 |
| 8,998,867 | B2 * | 4/2015 | Sabeti | A61F 5/4405 604/335 |
| 9,119,697 | B2 * | 9/2015 | Gobel | A61F 2/0013 |
| 10,441,455 | B2 * | 10/2019 | Eggert | A61F 5/4405 |
| 2003/0220621 | A1 * | 11/2003 | Arkinstall | A61F 5/445 604/335 |
| 2010/0069859 | A1 * | 3/2010 | Weig | A61F 5/445 604/335 |
| 2011/0015475 | A1 * | 1/2011 | Hanuka | A61F 2/04 600/32 |
| 2011/0092929 | A1 * | 4/2011 | Weig | A61F 5/445 604/338 |
| 2011/0218389 | A1 * | 9/2011 | Gobel | A61M 27/00 600/32 |
| 2011/0306823 | A1 * | 12/2011 | Gobel | A61F 2/0013 600/32 |
| 2012/0136324 | A1 * | 5/2012 | Hanuka | A61F 5/441 604/318 |
| 2013/0030397 | A1 * | 1/2013 | Sabeti | A61F 5/4405 604/338 |
| 2013/0060212 | A1 * | 3/2013 | Hanuka | A61F 5/4405 604/333 |
| 2013/0079737 | A1 | 3/2013 | Hanuka et al. | |
| 2013/0079738 | A1 | 3/2013 | Hanuka et al. | |
| 2013/0116642 | A1 | 5/2013 | Hanuka et al. | |
| 2013/0304008 | A1 * | 11/2013 | Hanuka | A61F 5/4405 604/338 |
| 2014/0163312 | A1 * | 6/2014 | Gobel | A61M 27/00 600/32 |
| 2015/0164679 | A1 * | 6/2015 | Maidl | A61F 5/445 604/332 |
| 2016/0287428 | A1 * | 10/2016 | Eggert | A61F 5/4405 |

FOREIGN PATENT DOCUMENTS

| | | |
|---|---|---|
| WO | WO2011/138728 | 11/2011 |
| WO | WO 2011/138728 | 11/2011 |
| WO | WO2014/008198 | 1/2014 |
| WO | WO 2014/008198 | 1/2014 |

* cited by examiner

CONTINENT OSTOMY VALVE AND METHOD OF USE

CLAIM OF PRIORITY

This application is a divisional of U.S. application Ser. No. 15/079,397, filed Mar. 24, 2016, which claims priority to U.S. Provisional Application Ser. No. 62/142,206, filed on Apr. 2, 2015, the entire contents of which are hereby incorporated by reference.

BACKGROUND

1. Technical Field

This document relates to ostomy devices. For example, this document relates to continent ostomy (e.g., continent ileostomy) valve devices.

2. Background Information

Treating some diseases of the digestive or urinary system can involve removing all or part of a patient's small intestine, colon, rectum, or bladder. In these cases, waste must be rerouted to exit the body of the subject. The rerouting surgery, known as an ostomy, can involve creating an opening in the abdominal wall so that a portion of the intestinal tract can be brought out to the skin level, resulting in what is called a stoma. Three common types of abdominal wall stomas result from, and may be classified as, a colostomy, ileostomy, and urostomy, which involve patients who have had surgery on their large intestine, small intestine, and urinary bladder, respectively. Typically, a medical prosthetic known as an ostomy pouching system can be used to collect waste from a diverted biological system as it exits a stoma. In a surgical variation of an ileostomy, a reservoir pouch is created inside the abdomen with a portion of the terminal ileum. A valve can be constructed in the pouch, and a stoma can be brought through the abdominal wall. A catheter or tube inserted into the pouch can be used drain feces from the reservoir.

SUMMARY

This document provides methods and materials related to ostomy devices, and particularly to valves for use with ostomies (e.g., ileostomies, including standard ileostomies and surgically created continent pouches). The devices provided herein may be readily inserted and removed by a user, and may be used to anchor a continent ostomy device in place without the use of inflation balloons. In addition, the valves provided herein may be useful with urostomy devices, colostomy devices, feeding tubes, G tubes, anal plugs, and enteral access devices in general. In some embodiments, the valve can be used as an anal plug for fecal incontinence, either for ambulatory patients (e.g., used as a plug that is removed to empty), or in patients who are bed-ridden (e.g., due to a spinal cord injury or other condition), where a care-giver can use the valve as a means to facilitate the bowel program or stool removal, mini-enema, etc. This document also provides devices that can engage a valve device as provided herein, and can be used to insert and remove the valve devices.

In one aspect, this document features an ostomy valve. The valve can include a hollow tubular member having a first end, a second end, an outer surface, an inner surface, and a lumen extending axially through the tubular member between the first and second ends; a sealing element contained within the lumen; and an anchoring element at or adjacent to the second end; where the ostomy valve is reversibly adjustable between a radially expanded configuration for retention in a stoma, and a non-radially expanded configuration for insertion into or removal from a stoma. The ostomy valve can further have a housing connected to the first end, where the housing defines an opening that is continuous with the lumen of the hollow tubular member. The sealing element can be contained within the opening of the housing. The hollow tubular member can contain high elongation tubing. The sealing element can contain silicone or isoprene. The sealing element can be configured to allow passage of a tube or catheter through the sealing element, and can effectively seal the valve after the tube or catheter is removed from the sealing element. The anchoring element can be defined by a widening of the hollow tubular member, such that a cross-sectional diameter of the hollow tubular member through the anchoring element is greater than a cross-sectional diameter of the hollow tubular member through the first end. The widening can include one or more fins defined by the outer surface of the hollow tubular member. The ostomy valve can further have one or more protrusions extending circumferentially around the outer surface of the hollow tubular member, where the one or more protrusions are configured to reduce the likelihood that mucous, waste, or other bodily fluids will leak from a stoma when the ostomy valve is seated in the stoma. The ostomy valve can have a length from the first end to the second end of about 1 cm to about 10 cm, and an external diameter of about 0.5 cm to about 2 cm, exclusive of the anchoring element.

In another aspect, this document features an insertion/removal device for use with an ostomy valve, such as the ostomy valve described herein. The insertion/removal device can include a hollow outer tube having a first end and a second end, where the first end is attached to a first handle; an inner shaft positioned axially and slidably within the hollow outer tube, where the inner shaft has a first end and a second end, where the first end is attached to a second handle, and where a portion of the inner shaft proximate to its first end passes through an opening in the first handle; an inflatable balloon positioned on an outer surface of the hollow outer tube distal to the first handle; and an inflation port in fluid communication with the inflatable balloon, where the inflation port extends from the inflatable balloon toward the first handle. Force exerted on the first and second handles to bring them closer together can cause the second end of the inner shaft to extend beyond the second end of the hollow outer tube. The second end of the inner shaft can define a protrusion configured to engage a complementary feature of the inner surface of a hollow tubular member of an ostomy valve as provided herein.

In another aspect, this document features an article of manufacture or kit containing packaging and one or more ostomy valves as described herein. The article of manufacture can further include an insertion/removal device as described herein.

In still another aspect, this document features an ostomy valve that includes a hollow tubular member having a first end, a second end, an outer surface, an inner surface, and a lumen extending axially through the tubular member between the first and second ends; a housing connected to the first end, where the housing defines an opening that is continuous with the lumen of the hollow tubular member; a sealing element contained within the lumen of the hollow tubular member or the opening of the housing; and an anchoring element at or adjacent to the second end; where the ostomy valve is reversibly adjustable between a radially expanded configuration for retention in a stoma, and a non-radially expanded configuration for insertion into or removal from a stoma. The sealing element can be contained within the opening of the housing. The hollow tubular member can include high elongation tubing. The sealing element can include silicone or isoprene. The sealing element can be configured to allow passage of a tube or catheter therethrough, and to effectively seal the valve after the tube or catheter is removed from the sealing element. The anchoring element can be defined by a widening of the hollow tubular member, such that a cross-sectional diameter of the hollow tubular member through the anchoring element is greater than a cross-sectional diameter of the hollow tubular member through the first end. The widening can include one or more fins defined by the outer surface of the hollow tubular member. The widening can include a portion of the outer surface of the hollow tubular member that is at an obtuse angle with respect to the outer surface at the first end of the hollow tubular member. The ostomy valve can further define one or more protrusions extending from the outer surface of the hollow tubular member, where the one or more protrusions are configured to reduce the likelihood that mucous, waste, or other bodily fluids will leak from a stoma when the ostomy valve is seated in the stoma. The one or more protrusions can extend circumferentially around the outer surface of the hollow tubular member. The ostomy valve can have a length from the first end to the second end of about 1 cm to about 10 cm, and an external diameter of about 0.5 cm to about 2 cm, exclusive of the anchoring element.

In another aspect, this document features an insertion/removal device for use with an ostomy valve as provided herein, where the insertion/removal device includes a hollow outer tube having a first end and a second end, where the first end is attached to a first handle; an inner shaft positioned axially and slidably within the hollow outer tube, where the inner shaft has a first end and a second end, where the first end is attached to a second handle, and where a portion of the inner shaft proximate to its first end passes through an opening in the first handle; an inflatable balloon positioned on an outer surface of the hollow outer tube distal to the first handle; and an inflation port in fluid communication with the inflatable balloon, where the inflation port extends from the inflatable balloon toward the first handle. Force exerted on the first and second handles to bring them closer together can cause the second end of the inner shaft to extend beyond the second end of the hollow outer tube. The second end of the inner shaft can define a protrusion configured to engage a complementary feature on the inner surface of an ostomy valve that includes a hollow tubular member having a first end, a second end, an outer surface, an inner surface, and a lumen extending axially through the tubular member between the first and second ends; a sealing element contained within the lumen; and an anchoring element at or adjacent to the second end, where the ostomy valve is reversibly adjustable between a radially expanded configuration for retention in a stoma, and a non-radially expanded configuration for insertion into or removal from a stoma. When the protrusion is engaged with the complementary feature, force exerted on the first and second handles to bring them closer together can cause the second end of the inner shaft to extend beyond the second end of the hollow outer tube, such that the ostomy valve elongates into a non-radially expanded configuration.

In yet another aspect, this document features an article of manufacture containing one or more ostomy valves and a packaging material, where each valve includes a hollow tubular member having a first end, a second end, an outer surface, an inner surface, and a lumen extending axially through the tubular member between the first and second ends; a sealing element contained within the lumen; and an anchoring element at or adjacent to the second end, where each ostomy valve is reversibly adjustable between a radially expanded configuration for retention in a stoma, and a non-radially expanded configuration for insertion into or removal from a stoma. Each ostomy valve can have a length from the first end to the second end of about 1 cm to about 10 cm, and an external diameter of about 0.5 cm to about 2 cm, exclusive of the anchoring element. The article of manufacture can further include an insertion/removal device that has a hollow outer tube with a first end and a second end, where the first end is attached to a first handle; an inner shaft positioned axially and slidably within the hollow outer tube, where the inner shaft has a first end and a second end, where the first end is attached to a second handle, and where a portion of the inner shaft proximate to its first end passes through an opening in the first handle; an inflatable balloon positioned on an outer surface of the hollow outer tube distal to the first handle; and an inflation port in fluid communication with the inflatable balloon, where the inflation port extends from the inflatable balloon toward the first handle. The second end of the inner shaft of the insertion/removal device can define a protrusion configured to engage a complementary feature on the inner surface of the one or more ostomy devices.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1A:
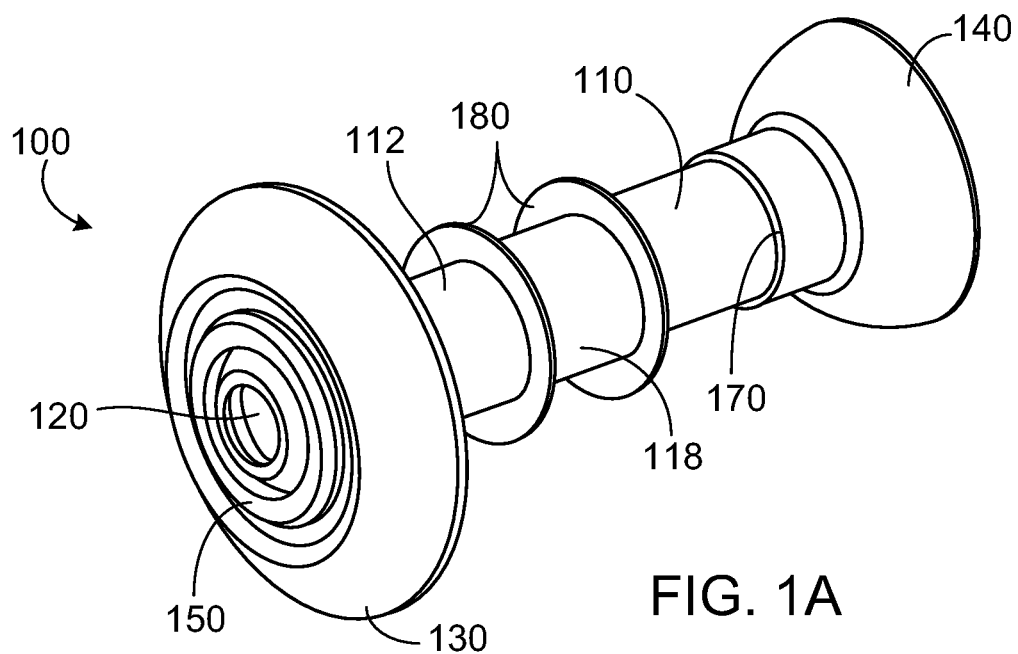
FIG. 1A is a perspective view of an embodiment of a valve device as provided herein.

This document provides methods and materials related to ostomy devices. For example, this document provides valve devices that can provide a route for accessing an abdominal reservoir pouch, and can be used to anchor a continent ostomy device in place without the use of inflation balloons. The devices and methods provided herein can be used to effectively seal a stoma opening and prevent waste material and/or gas from escaping a waste reservoir of an ostomy patient.

In general, this document features a self-collapsing device that can be inserted by a user through a stoma in a gentle manner that minimizes damage and trauma to tissue. When deployed, the device can remain firmly in place, without the risks of deflation or over inflation that might be encountered with a device having a balloon. The devices provided herein also can be readily removed from the stoma, with minimal (e.g., no) harm to the tissue.

With reference to FIGS. 1A-1L, a valve device 100 can include a tubular member 110, a sealing element 120, a stoma cover 130, and an anchoring element 140. In some embodiments, a device 100 also can have one or more of: a housing 150 for the sealing element 120, a nose piece 160, and a grip 170. In some embodiments, the device 100 also can have one or more ribs 180.

With respect to FIGS. 1A-1D, the tubular member 110 can have a proximal portion 112, a distal portion 114, and a lumen extending axially therethrough such that the tubular member 110 has an interior surface 116, and an exterior surface 118.

The sealing element 120 can be located within the proximal portion of the tubular member 110, although it is to be noted that a sealing element could be located anywhere within the tubular member 110. In some embodiments, a device as provided herein may include more than one (e.g., two or three) sealing elements. In some embodiments, the device 100 can include the housing 150, with the sealing element 120 positioned therein. When the housing 150 is present, it defines an opening therethrough that is in fluid communication with the lumen of the tubular member 110. The sealing element 120 can be retained within the tubular member 110 or the housing 150 by one or more collars (e.g., collar 152), which can be formed as part of the housing 150, for example. The sealing element 120 can contain or be made from a material such as silicone, polyurethane, latex, or isoprene, such that it can allow passage of a catheter or tube through the tubular member 110, but will effectively provide a seal once the catheter or tube has been removed from the tubular member 110.

Figure 1B:
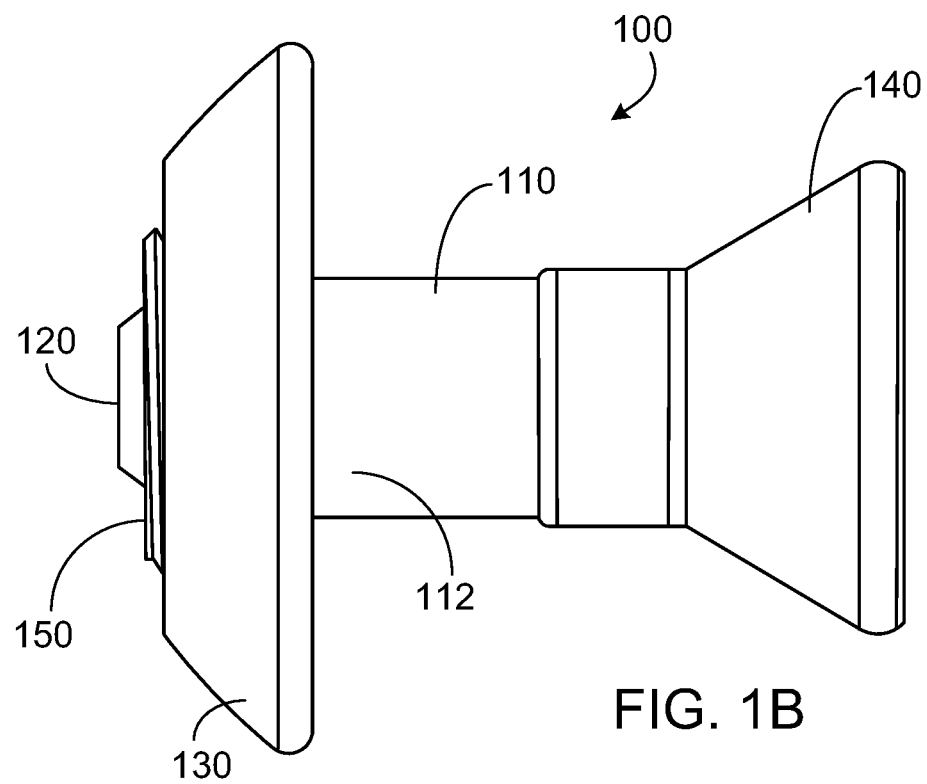
FIG. 1B is a side view of an embodiment of a valve device as provided herein.
Figure 1C:
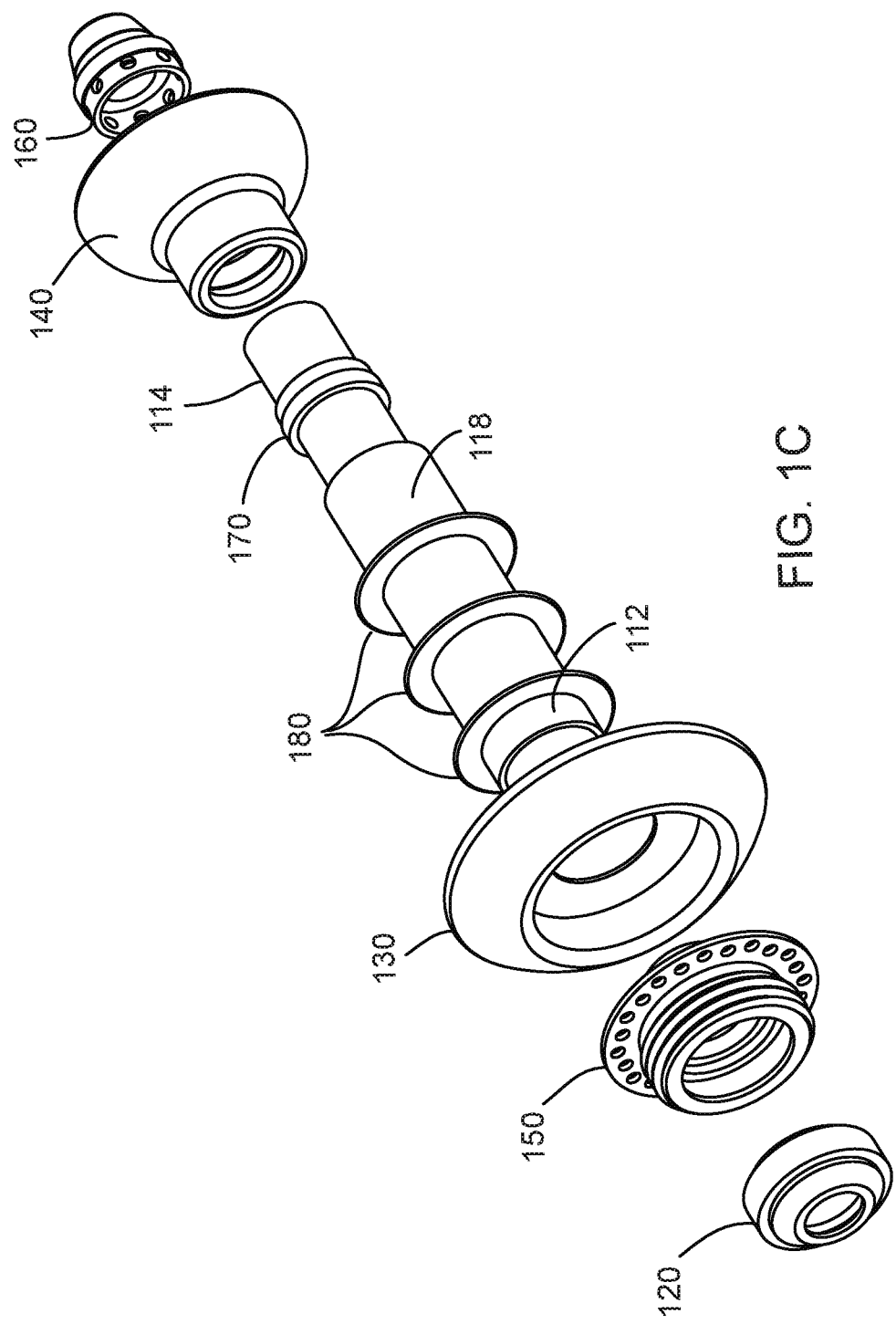
FIG. 1C is an exploded perspective view of an embodiment of a valve device as provided herein.
Figure 1D:
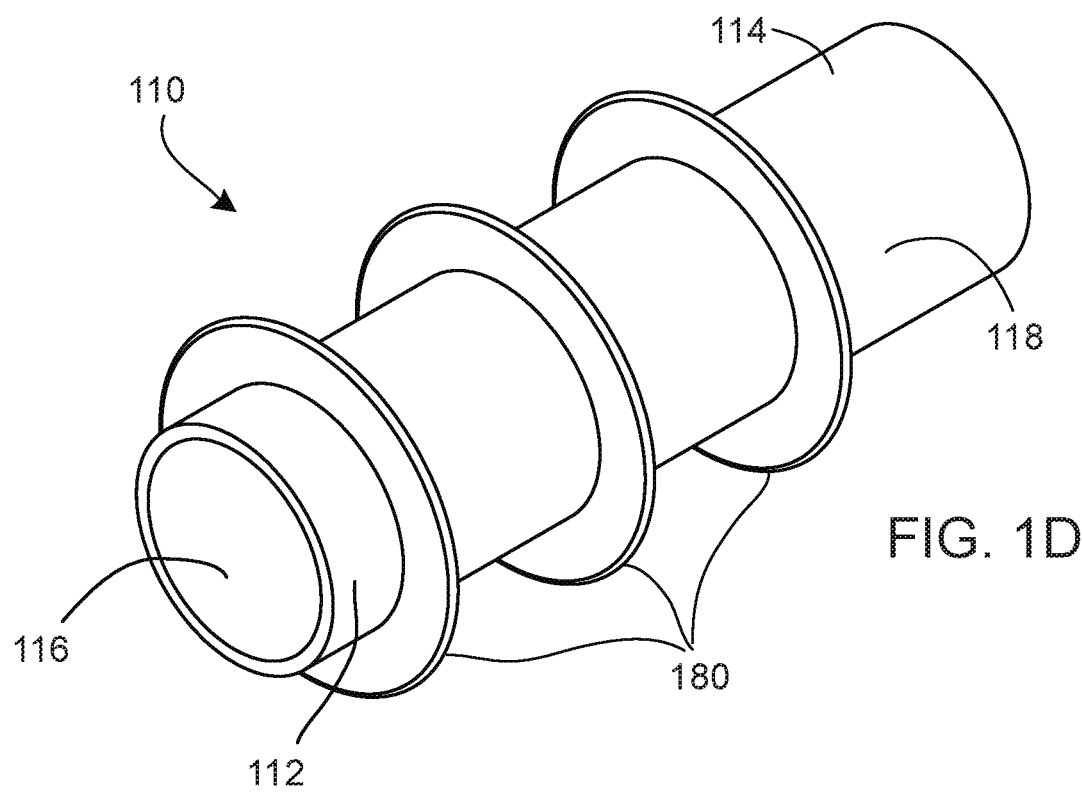
FIG. 1D is a perspective view of an embodiment of the tubular member of a valve device as provided herein.
Figures 1E, 1F:
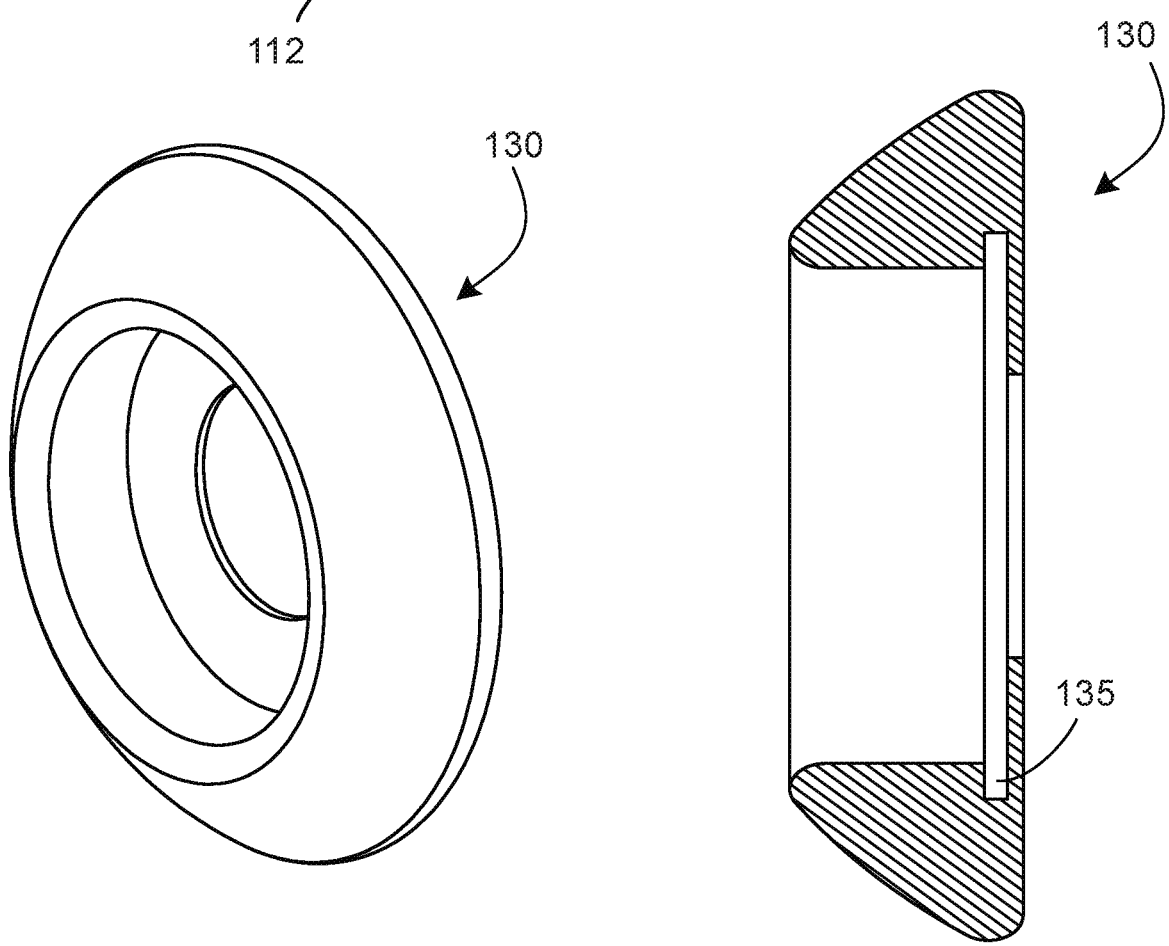
FIG. 1E is a perspective view of an embodiment of the stoma cover of a valve device as provided herein.
FIG. 1F is a cross-sectional side view of the stoma cover depicted in FIG. 1E.
Figure 1G:
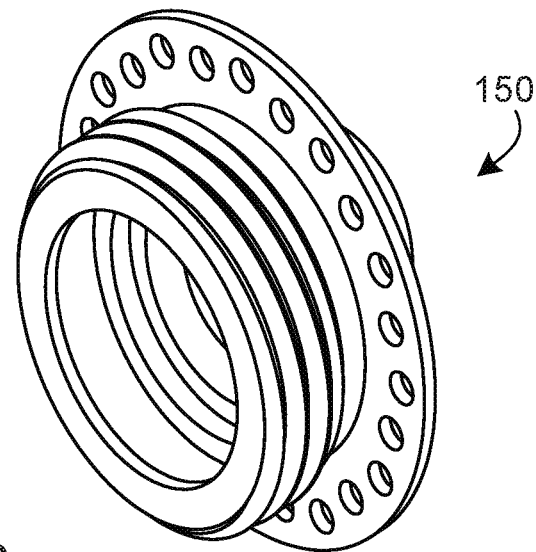
FIG. 1G is a perspective view of an embodiment of the housing of a valve device as provided herein.
Figure 1H:
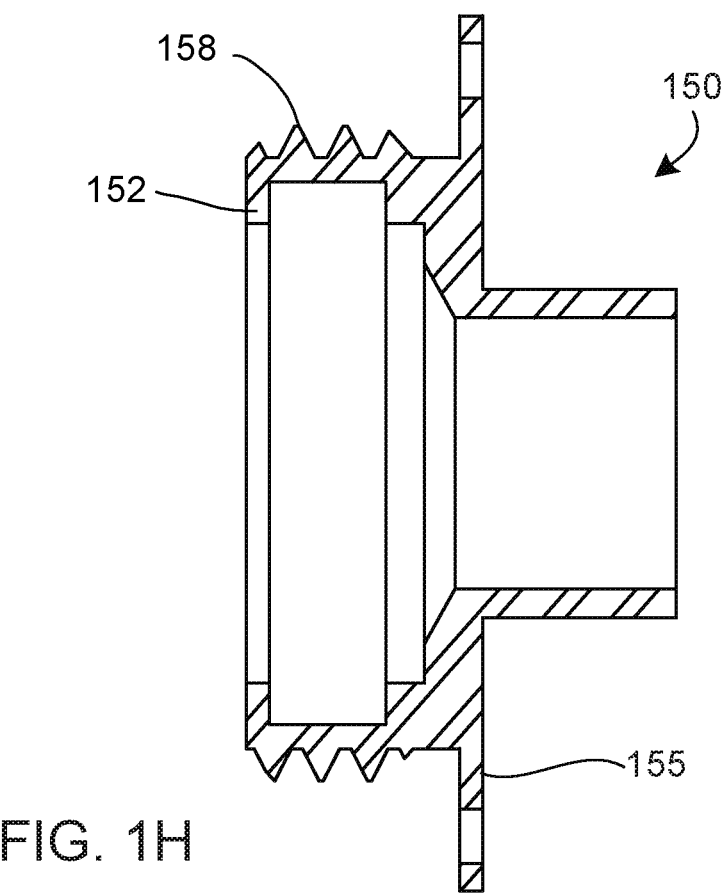
FIG. 1H is a cross-sectional view of the housing depicted in FIG. 1G.
Figure 1I:
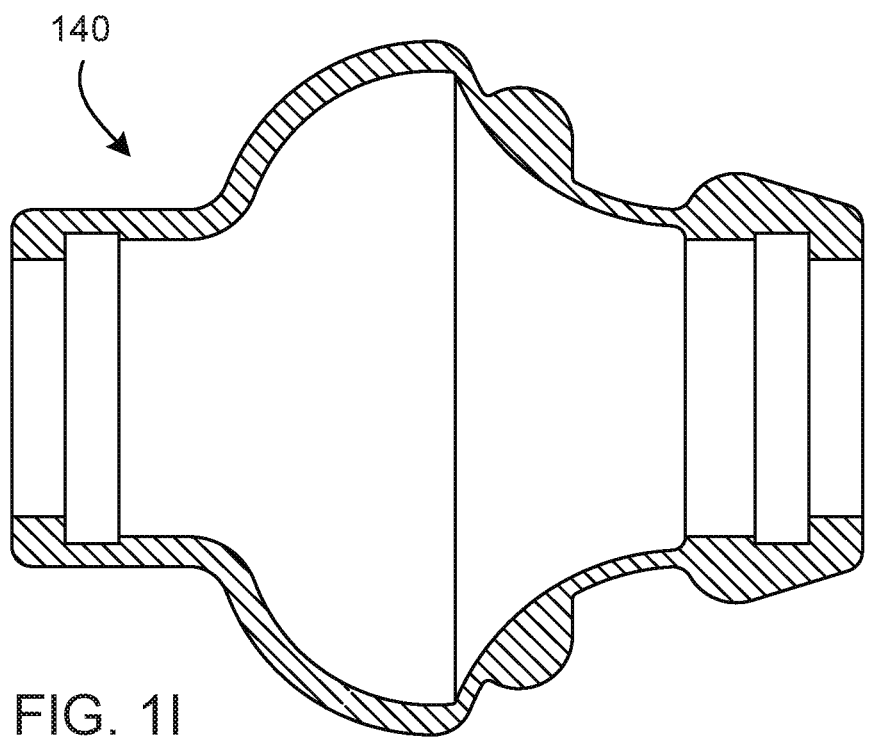
FIG. 1I is a cross-sectional view of an embodiment of an anchoring element of a valve device as provided herein.
Figure 1J:
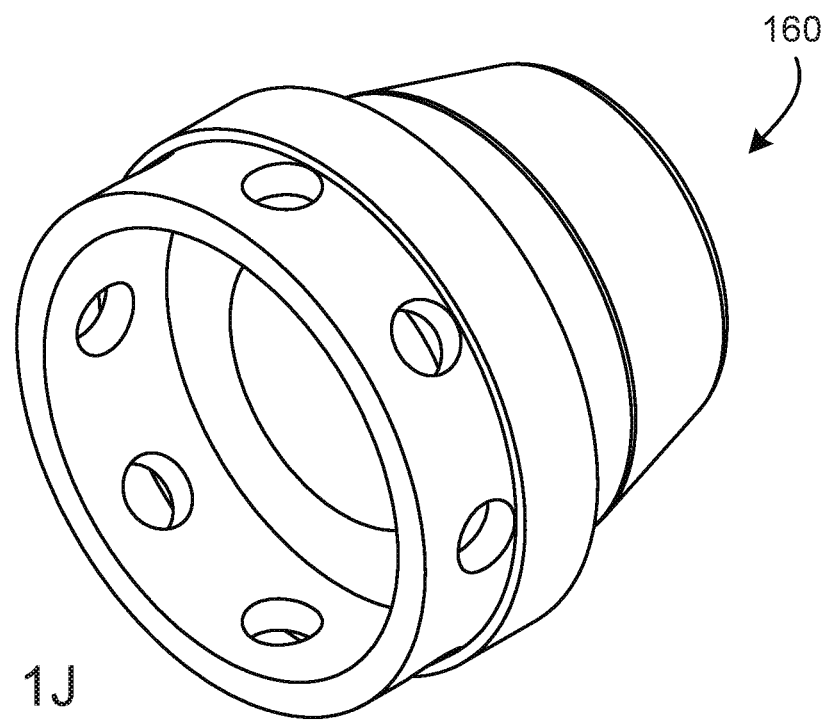
FIG. 1J is a perspective view of an embodiment of the nose of a valve device as provided herein.

With reference to FIGS. 1A-1C, 1E, 1F, and 1K, the stoma cover 130 can be located at or adapted to attach to the proximal portion 112 of the device 100. In some embodiments, as depicted in FIGS. 1A-1C, for example, the stoma cover 130 can extend circumferentially around the proximal portion 112 of the tubular member 110 or around the housing 150. In some embodiments, the housing 150 can define threads or another structure to facilitate engagement of the housing 150 with the stoma cover 130. For example, the housing 150 depicted in FIGS. 1G and 1H defines threads 158, which can be adapted to engage the stoma cover 130.

Figure 1K:
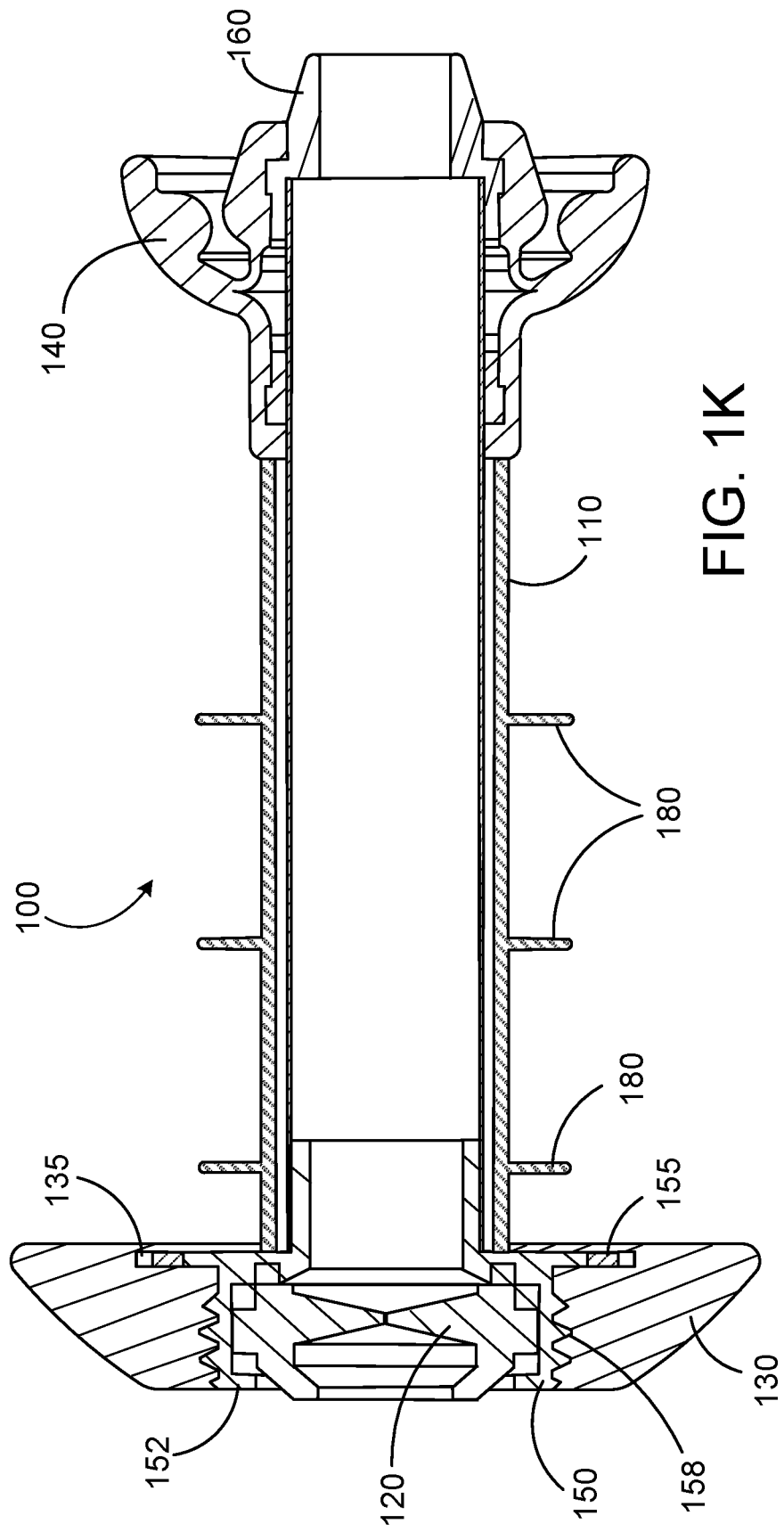
FIG. 1K is a cross-sectional view of an embodiment of a valve device as provided herein.

The stoma cover 130 can be adapted for removable attachment to the proximal portion 112 of the tubular member 110. In some embodiments, the stoma cover 130 can be made from a material that is capable of absorbing mucous and other fluids that may leak from the stoma. For example, the stoma cover 130 can be made from an absorbent, disposable material such as bamboo, polyester, hemp, polypropylene, or any diaper material. In some embodiments, the stoma cover 130 can have layers of material that can wick away and then absorb mucous and fluid. When the stoma cover 130 becomes soiled by mucous or other bodily fluids, it can be removed and replaced by a user. In some embodiments, the material from which the stoma cover 130 is made can be flexible, which can aid in installation and removal of the stoma cover 130. The stoma cover 130 can be held in place by one or more collars or other protrusions that can extend from the exterior surface 118 of the tubular member 110 or the housing 150. As depicted in FIG. 1K, for example, the stoma cover 130 can be held in place on the housing 150 by a circumferential ring 155, which can be configured to fit into a groove 135 on the stoma cover 130.

With reference to FIGS. 1A-1C, 1I, and 1K, the anchoring element 140 can be located at the distal portion 114 of the tubular member 110. In some embodiments, the anchoring element 140 can comprise part or all of the distal portion 114 of the tubular member 110. In some embodiments, the anchoring element 140 can be constructed separately from the tubular member 110, such that it is adapted for attachment to the distal portion 114 of the tubular member 110. The anchoring element 140 can define an opening therethrough, such that it is in fluid communication with the lumen of the tubular member 110.

In some embodiments, when the anchoring element 140 is separately constructed from the tubular member 110, the external surface 118 of the tubular member 110, or the internal surface of the anchoring element 140, can include a structure to facilitate secure attachment of the anchoring element 140 to the distal portion 114 of the tubular member 110. For example, the device 100 can have a circumferential grip 170 on the external surface 118 of the tubular member 110, which can contact the internal surface of the anchoring element 140 when it is engaged with the tubular member 110. The grip 170 can be made from the same material as the tubular member 110, or can include a different material (e.g., a resin or thermoplastic material such as polyetherimide).

The anchoring element 140 can be configured such that it has a greater external (cross-sectional) diameter than the proximal portion 112 of the tubular member 110. Such a configuration can provide a mechanism for holding the anchoring element 140 firmly against the interior wall of the remaining intestine or a waste reservoir within a user, adjacent to the user's internal abdominal wall.

In some embodiments, the tubular member 110 can be extendable and retractable, such that its length can be adjusted depending on the length of a user's stoma. Thus, when the device 100 is in place, the stoma cover 130 can be positioned against the user's external abdominal wall around the periphery of the stoma, and the anchoring element 140 can be positioned against the interior wall of the remaining intestine or the waste reservoir to hold it against the user's internal abdominal wall. In some embodiments, the tubular member 110 can include or be made from high elongation tubing, or can include two or more nested sections of tubing that can telescope to elongate or shorten the tubular member 110. As used herein, "high elongation" tubing has at least 30% (e.g., at least 35%, 40% or 45%) elastic elongation. High elongation tubing can contain, for example, silicone, latex, isoprene, or polyurethane-based material. In some embodiments, if the anchoring element 140 is constructed separately from the tubing member 110 and is attached at the distal portion 114 of the tubing member 110, the anchoring element 140 and the tubular member 110 can telescope relative to one another.

Figure 1L:
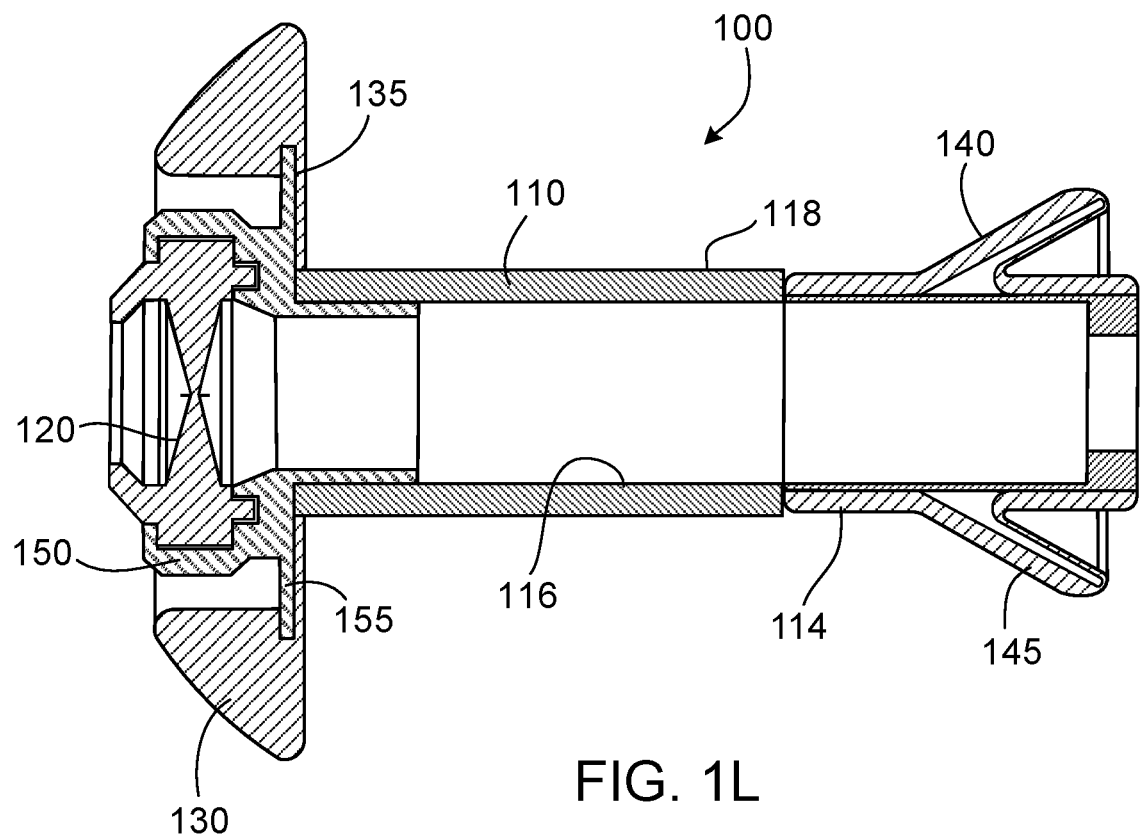
FIG. 1L is a cross-sectional view of another embodiment of a valve device as provided herein.

Any of a number of suitable means can be used to achieve a configuration in which the anchoring element 140 has a greater external diameter than the proximal portion 112 of the tubular member 110. As shown in FIG. 1L, for example, the distal portion 114 of the tubular member 110 can define one or more fins, such as the fin 145. The fin 145 can be formed from a folded portion of the material from which the tubular member 110 is made. Such a configuration can allow the fin 145 to become unfolded as the device 100 is elongated (e.g., by a user or a clinician), thus lowering the profile of the anchoring element 140 and facilitating insertion of the device 100 into and through a stoma. An elongated configuration of an ostomy device in which the anchoring element has a lower profile is referred to herein as a "non-radially expanded" configuration, while a configuration in which the anchoring element has a higher profile is referred to herein as a "radially expanded" configuration. Methods for inserting or removing a valve device as provided herein are described below, as are methods for retracting a valve device to be in a shortened (e.g., "original") configuration for retention in a stoma.

Figure 2A:
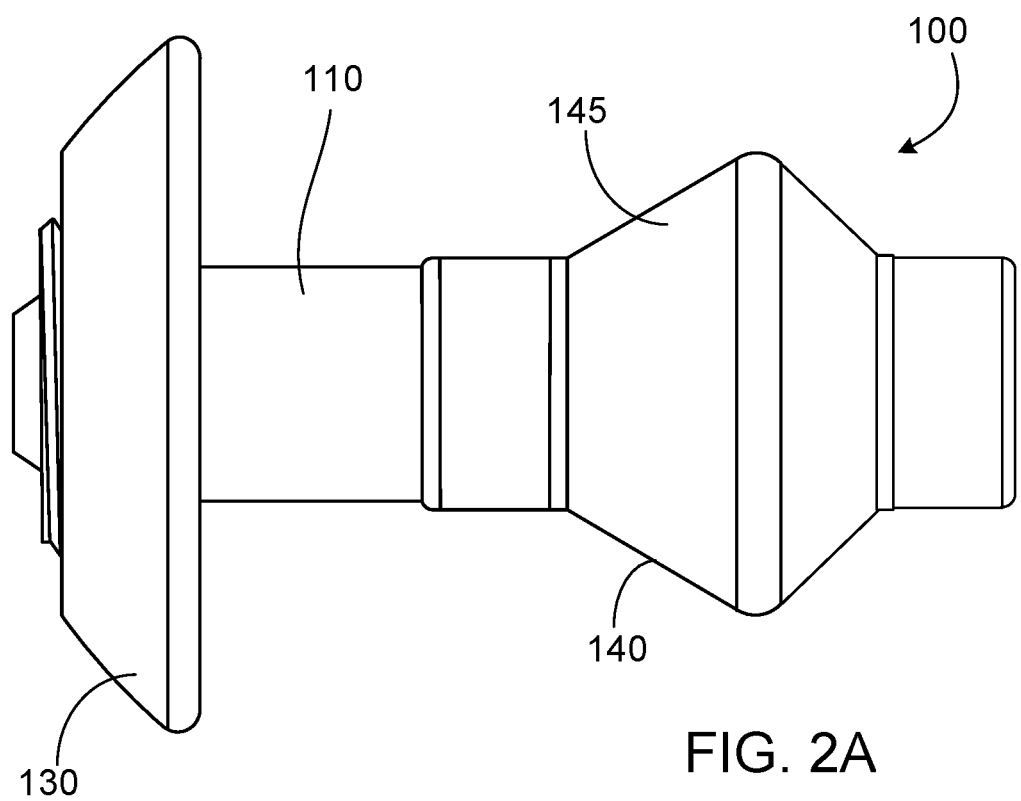
FIG. 2A is a side view of an embodiment of a valve device as provided herein, in an extended configuration.
Figure 2B:
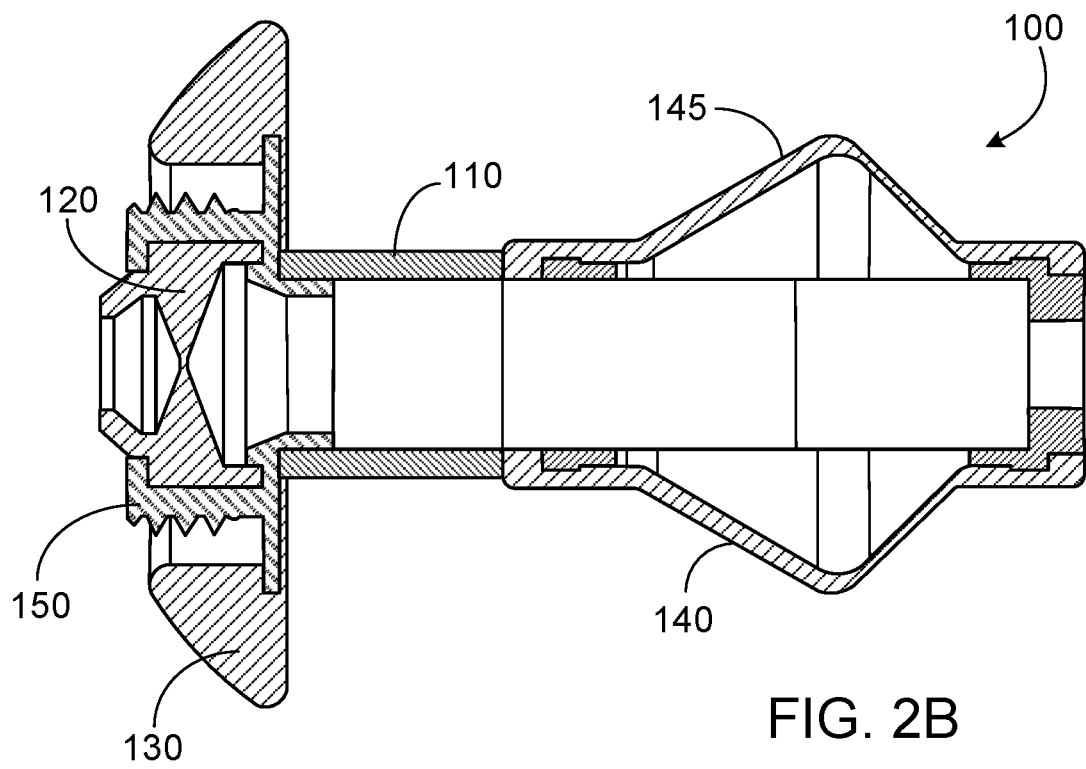
FIG. 2B is a cross-sectional view of an embodiment of a valve device as provided herein, in an extended configuration.

As depicted in FIG. 2A, the fin 145 can be angled such that a portion of the exterior surface 118 that forms the fin 145 is at an obtuse angle with respect to the exterior surface 118 at the proximal portion 112 of the tubular member 110. The exemplary embodiments of FIGS. 2A and 2B depict a device 100 having a fin 145 formed from a folded portion of the tubular member 110, in partially extended form. In some embodiments, when the device 100 is in a fully extended, non-radially expanded configuration, the fin 145 can be completely unfolded such that the external diameter of the tubular member 110 is essentially constant along its axial length. In some embodiments, when the device 100 is in a fully extended configuration, the diameter of the distal portion 114 of the tubular member 110 may still be greater than the cross-sectional diameter of the proximal portion 112, but the difference between the diameters can be decreased to an extent that the device 100 can be readily inserted or removed from a stoma by a user.

Figure 3A:
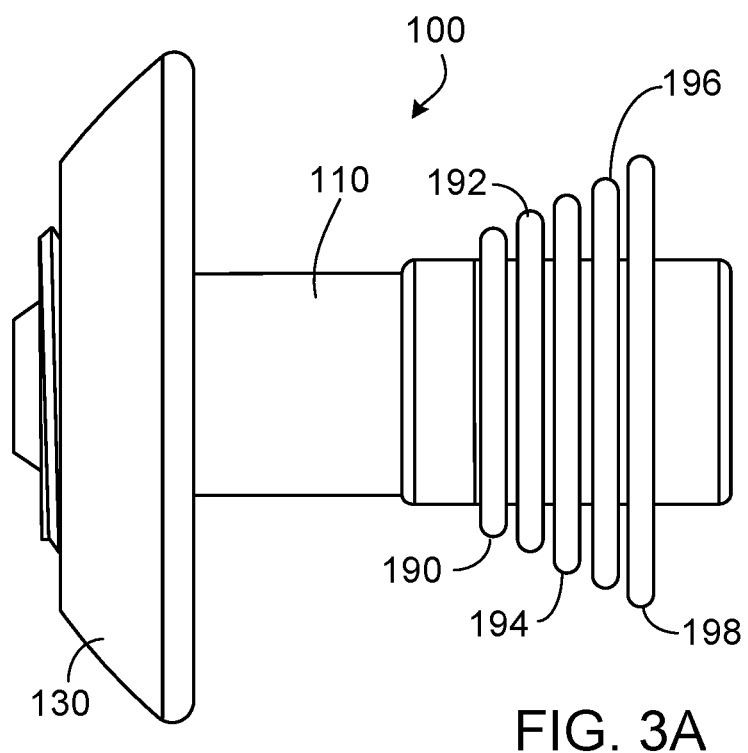
FIG. 3A is a side view of an embodiment of a valve device as provided herein.
Figure 3B:
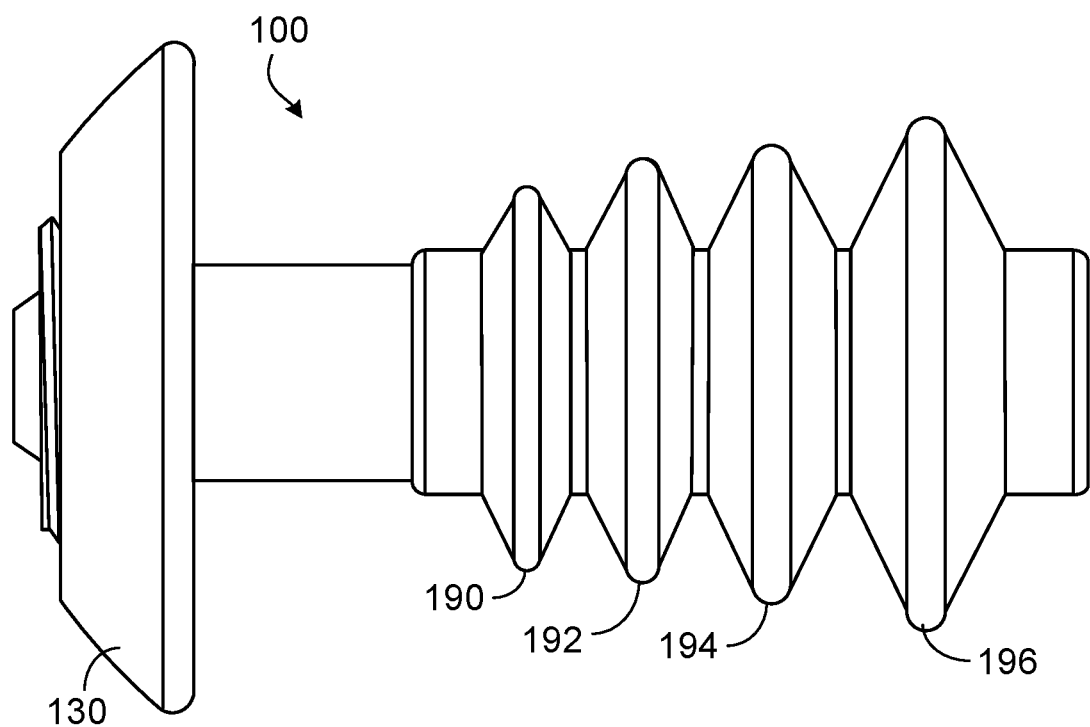
FIG. 3B is a side view of an embodiment of a valve device as provided herein, in an extended configuration.

In some embodiments, an anchoring element of a device as provided herein can include more than one (e.g., two, three, four, five, or more than five) fins or other structures to achieve an anchoring configuration. For example, the valve devices shown in FIGS. 3A and 3B have anchoring elements with four or five fins. FIG. 3A shows the device 100 having five fins (190, 192, 194, 196, and 198). In some embodiments, the fins 190, 192, 194, 196, and 198 can be formed from folded portions of the material from which the tubular member 110 is made. Fins 190, 192, 194, 196, and 198 can be of increasing size such that they extend progressively further from the axial exterior surface 118 of the tubular member 110, resulting in a distal portion 114 that has a gradually greater external diameter than the proximal portion 112. The device 100 depicted in FIG. 3B has fins 190, 192, 194, and 196, which as shown are in an at least partially unfolded state such that the device 100 is in an extended configuration. In some embodiments, when the device 100 is in a fully extended configuration, the fins 190, 192, 194, and 196 can be completely unfolded such that the diameter of the tubular member 110 is essentially constant along its axial length. In some embodiments, when the device 100 is in a fully extended configuration, the diameter of the distal portion 114 of the tubular member 110 may still be greater than the diameter of the proximal portion 112, but the difference between the diameters can be decreased to an extent that the device 100 can be readily inserted or removed from a stoma by a user.

In some embodiments, a valve device as provided herein can include a nose piece 160 (FIGS. 1C and 1J), which can be positioned at or attached to the distal portion 114 of the tubular member 110, or connected to the anchoring element 140 at a distal portion of the device 100.

Figure 4:
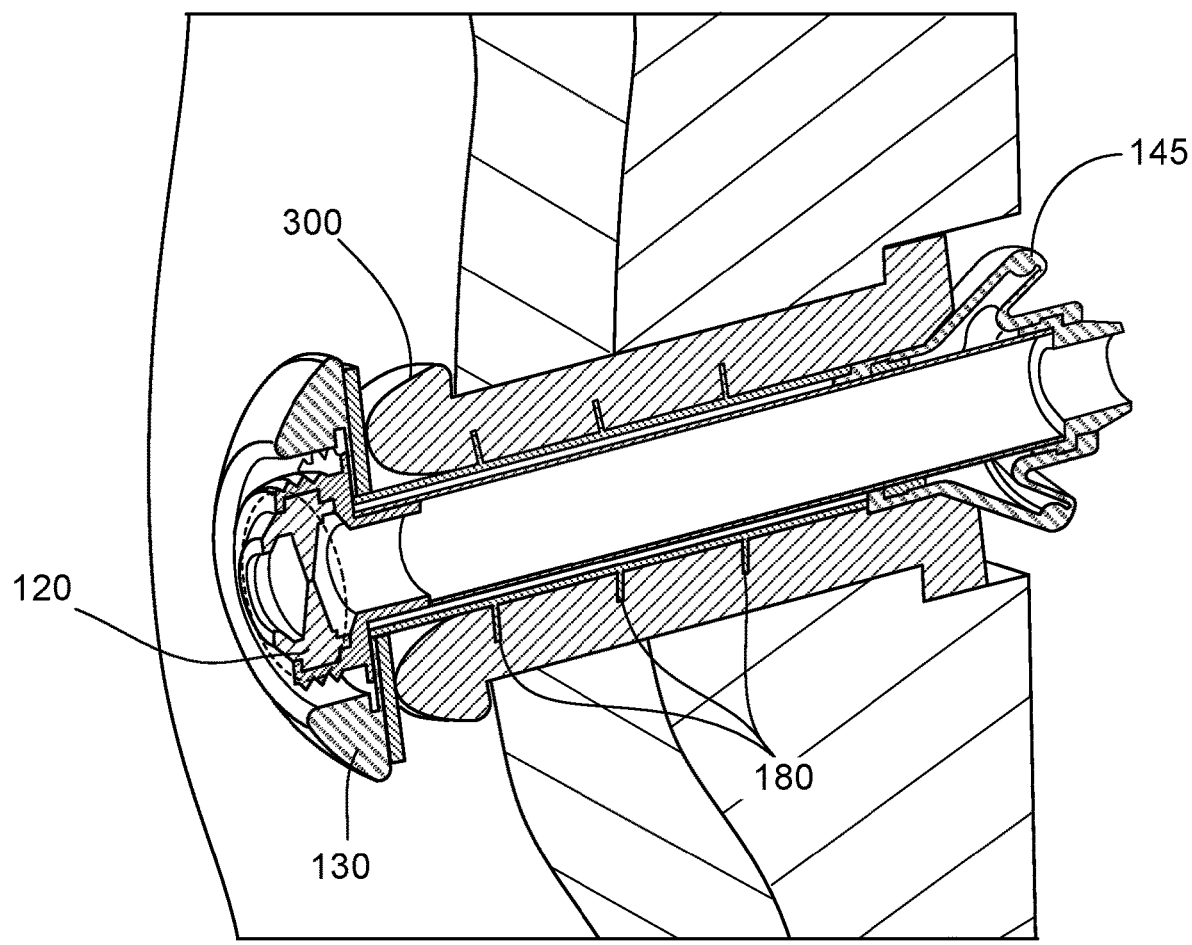
FIG. 4 is a cross-sectional view of an embodiment of a valve device as provided herein, positioned within a stoma.

It is to be noted that a device as provided herein can include any suitable number of fins, ribs, or "wipers," or other elements that can, in addition to holding the device in place within the stoma of a user, serve to reduce the likelihood of mucous or other bodily fluids from leaking out through the stoma around the device 100. Such elements can be integrally formed as part of the exterior surface 118 of the tubular member 110, or can be elements that are formed separately from the tubular member 110 and are held in place on the exterior surface 118 of the tubular member 110 by, for example, a friction fit, an elastic fit, or by seating in a groove or depression on the exterior surface 118. As an example, the device 100 shown in FIGS. 1A and 4 can have the fin 145, as well as circumferential ribs 180. The ribs 180 can contact the surface of a stoma 300 within the abdominal wall, and can prevent mucous or waste from leaking out of the stoma 300 along the valve device 100. The ribs 180 can be made from a material such as, for example, silicone, latex, polyurethane, or isoprene.

Figure 5A:
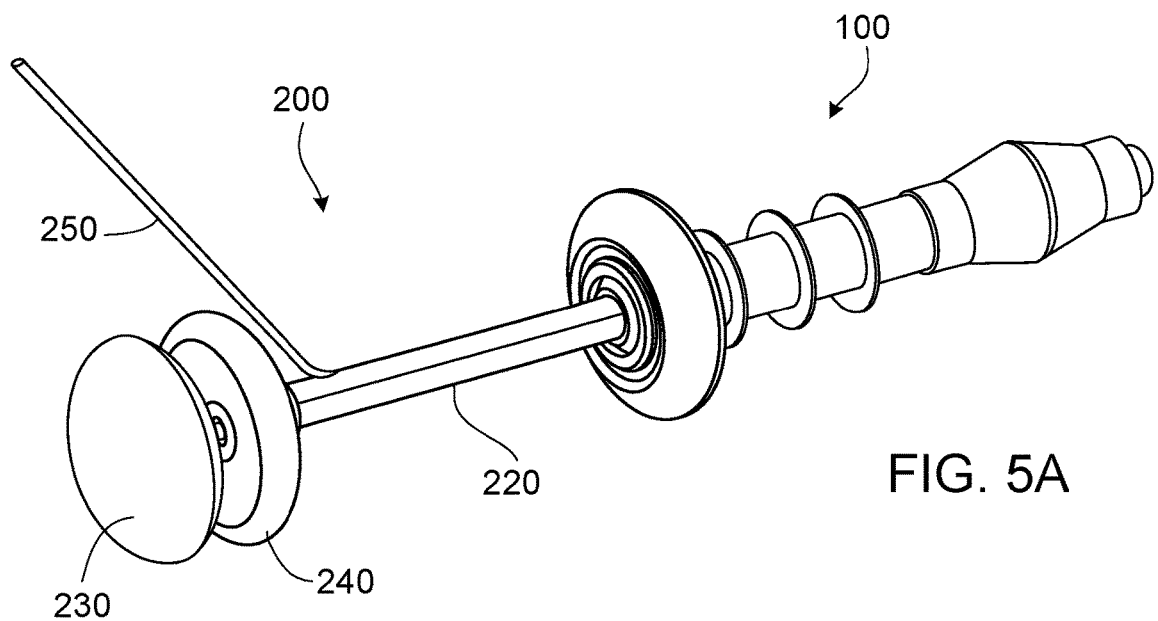
FIG. 5A is a perspective view of an embodiment of an insertion/removal device as provided herein, engaged with an embodiment of a valve device as provided herein.
Figure 5B:
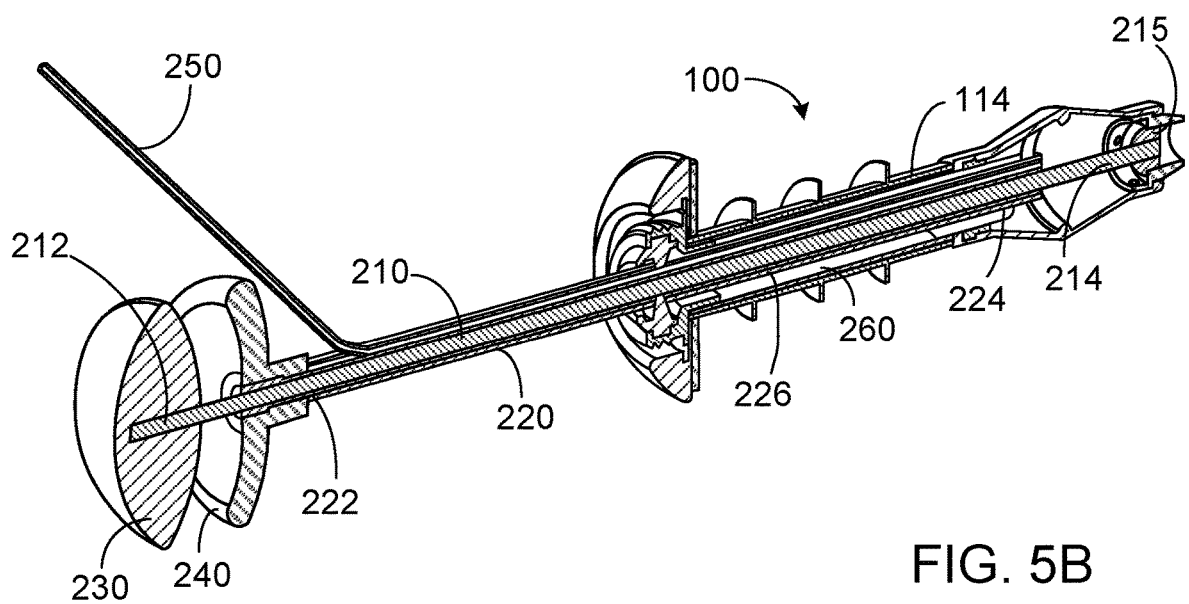
FIG. 5B is a cross-sectional view of an embodiment of an insertion/removal device as provided herein, engaged with an embodiment of a valve device as provided herein.

This document also provides tools that can be used to extend or retract a valve device as provided herein, and can be used for insertion of a valve device into a stoma, continent placement of a valve device in a stoma, and removal of a valve device from a stoma. An embodiment of such a tool is depicted in FIGS. 5A and 5B. The insertion/removal device 200 can have an inner shaft 210 that is slidably and coaxially contained within a hollow outer shaft 220. The inner shaft 210 can have a proximal portion 212 connected to a handle 230, and a distal portion 214. The hollow outer shaft 220 can have a proximal portion 222 connected to a handle 240, and a distal portion 224. The inner shaft 210 can be longer than the hollow outer shaft 220, such that it extends through an opening in the handle 240 before connecting to the handle 230. The distal portion 214 of the inner shaft 210 can have (e.g., can define or be connected to) one or more structures (e.g., the paddle 215) configured to engage a corresponding structure on the interior surface 116 of the distal portion 114 of the tubular member 110 (e.g., the ridge 115). In some embodiments, for example, a structure such as the paddle 215 can be inserted into the distal portion 114 of the tubular member 110, and then rotated or snapped into place such that it engages the ridge 115. The insertion/removal device 200 also can have an inflation port 250 that is in fluid communication with the interior of a balloon 260 on an exterior surface 226 of the hollow outer shaft 220. The balloon 260, when inflated, can hold the hollow outer shaft 220 of the insertion/removal device 200 firmly within the tubular member 110 of the valve device 100.

FIGS. 5A and 5B depict an embodiment of an insertion/removal device in use to extend a valve device. The insertion/removal device 200 is inserted into the tubular member 110 of the device 100 via the sealing element 120, and the paddle 215 is engaged with the ridge 115 within the distal portion 114 of the tubular member 110. Fluid passed through the inflation port 250 is used to inflate the balloon 260, which can hold the insertion/removal device 200 securely within the valve device. Force exerted on the handles 230 and 240 by a user or clinician pushes the handle 230 closer to the handle 240 and/or pulls the handle 240 closer to the handle 230, such that the distal portion 214 of the inner shaft 210 is extended beyond the distal portion 224 of the hollow outer shaft 220. Due to the interaction between the paddle 215 and the ridge 115, the actuation of the handles 230 and 240 causes the valve device 100 to elongate, as shown in FIGS. 5A and 5B. The elongated, non-radially expanded device 100 then can be inserted or removed from a stoma.

Figure 6A:
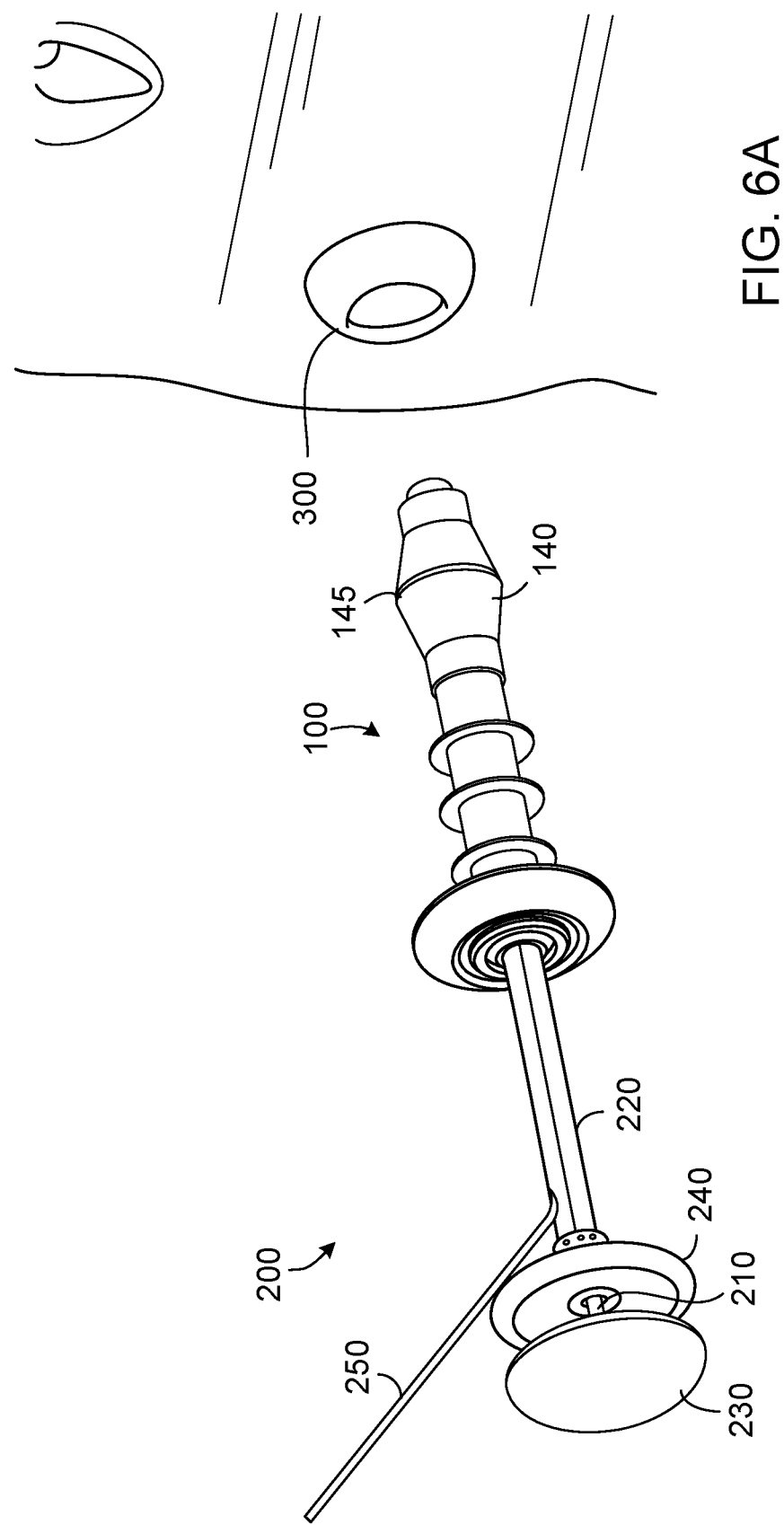
FIG. 6A is a perspective view of an embodiment of an insertion/removal device as provided herein, engaged with an embodiment of a valve device as provided herein, and positioned near a stoma.
Figure 6B:
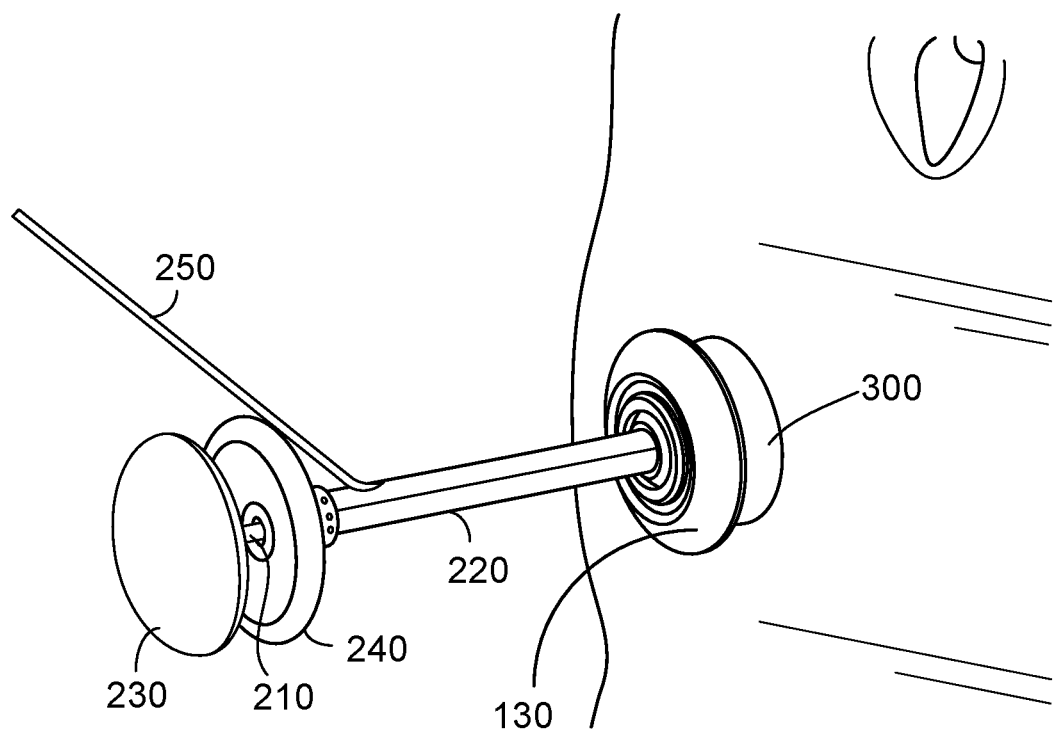
FIG. 6B is a perspective view of an embodiment of an insertion/removal device as provided herein, engaged with an embodiment of a valve device as provided herein, with the valve device positioned within a stoma.
Figure 6C:
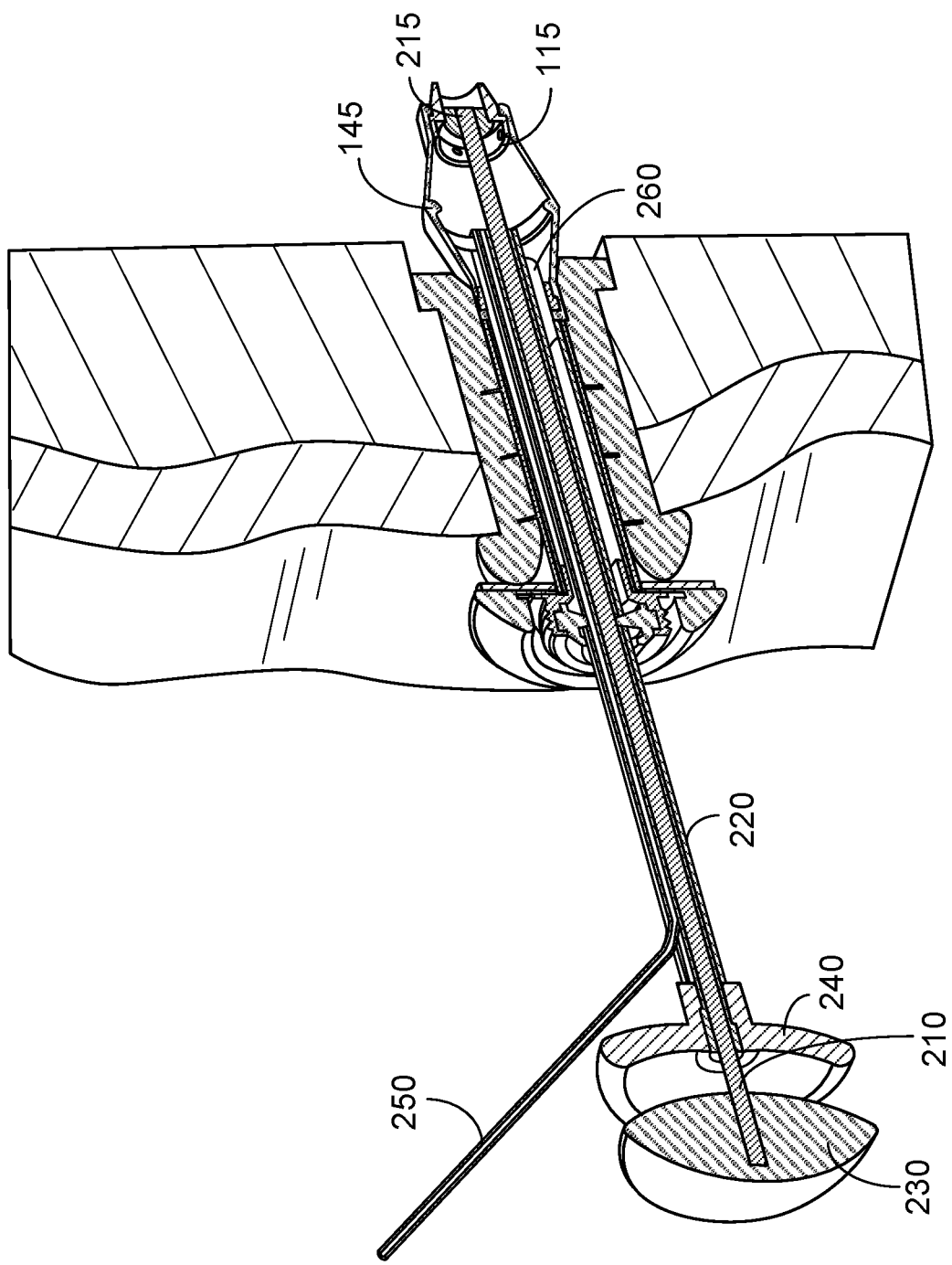
FIG. 6C is a cross-sectional view of an embodiment of an insertion/removal device as provided herein, engaged with an embodiment of a valve device as provided herein, with the valve device positioned within a stoma.

FIGS. 6A-6C depict the insertion of the valve device 100 into a stoma 300, while engaged with the insertion/removal device 200. In FIG. 6A, the devices 100 and 200 are in position to be inserted into the stoma 300. In FIGS. 6B and 6C, the devices 100 and 200 have been inserted into the stoma 300, and the insertion/removal device 200 remains engaged with the valve device 100, which is still in an extended configuration.

Figure 7A:
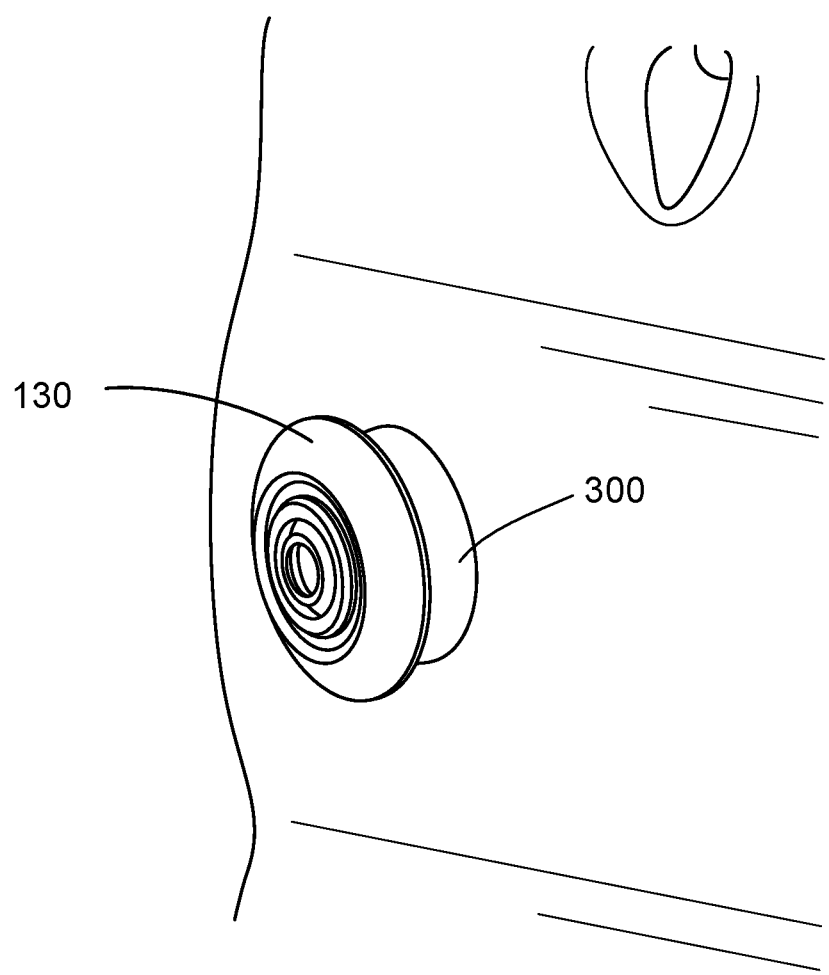
FIG. 7A is a perspective view of an embodiment of a valve device as provided herein, positioned within a stoma.
Figure 7B:
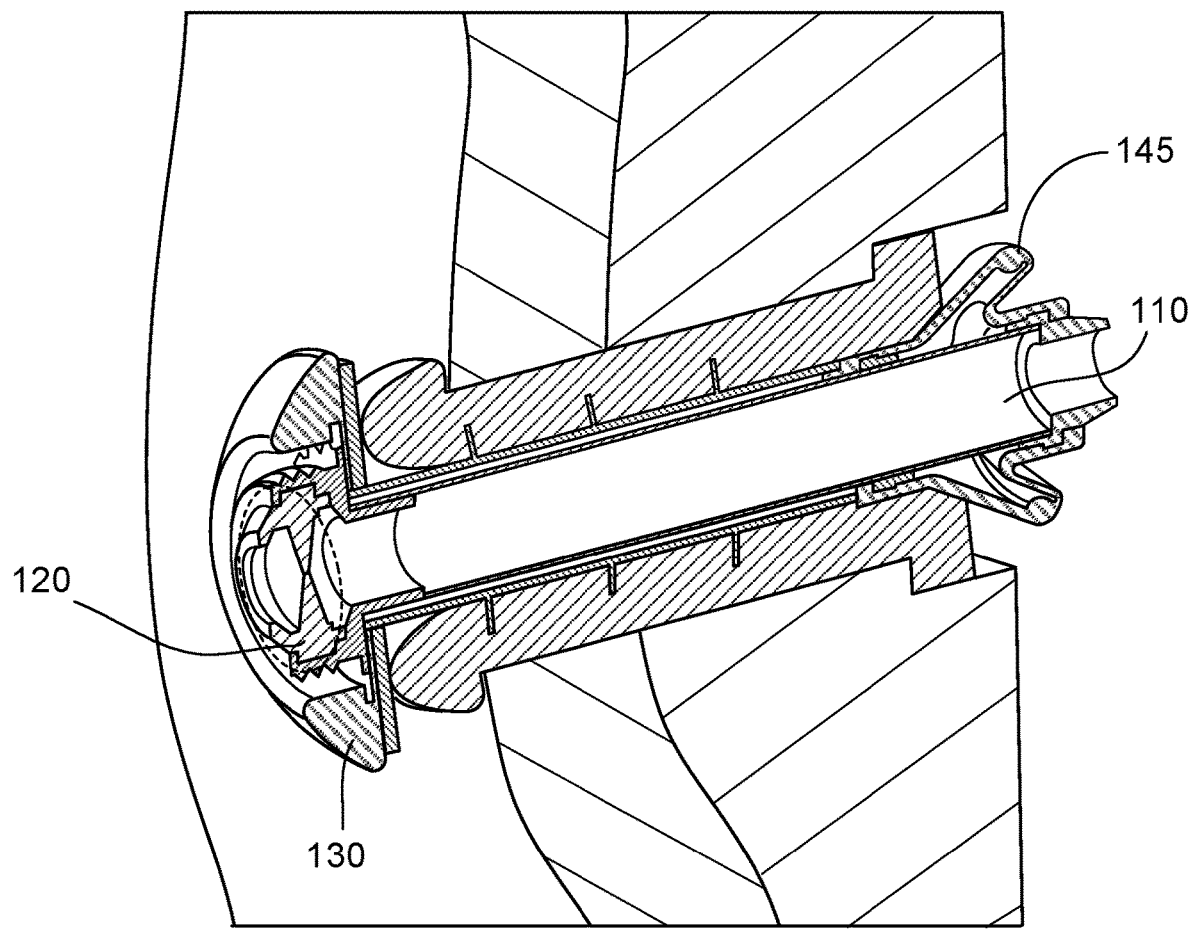
FIG. 7B is a cross-sectional view of an embodiment of a valve device as provided herein, positioned within a stoma.

FIGS. 7A and 7B show the valve device 100 seated in the stoma 300, after the insertion/removal device 200 has been removed. Before removal of the insertion/removal device 200, force exerted on the handles 230 and 240 by a user or clinician moves the handles 230 and 240 away from each other, such that the distal portion 214 of the inner shaft 210 moves toward the distal portion 224 of the hollow outer shaft 220. Since the inner shaft 220 is engaged with the distal portion 114 of the tubular member 110, via the interaction between the paddle 215 and the ridge 115, the movement of the inner shaft 210 causes the tubular member 110 to shorten, such that the distance between the distal portion 114 and the proximal portion 112 is reduced, and the valve device 100 "cinches" together for secure retention of the valve device 100 in the stoma 300. The balloon 260 can be deflated and the insertion/removal device 200 can be removed from the valve device 100 via the sealing element 120, rendering the user continent.

Figure 8A:
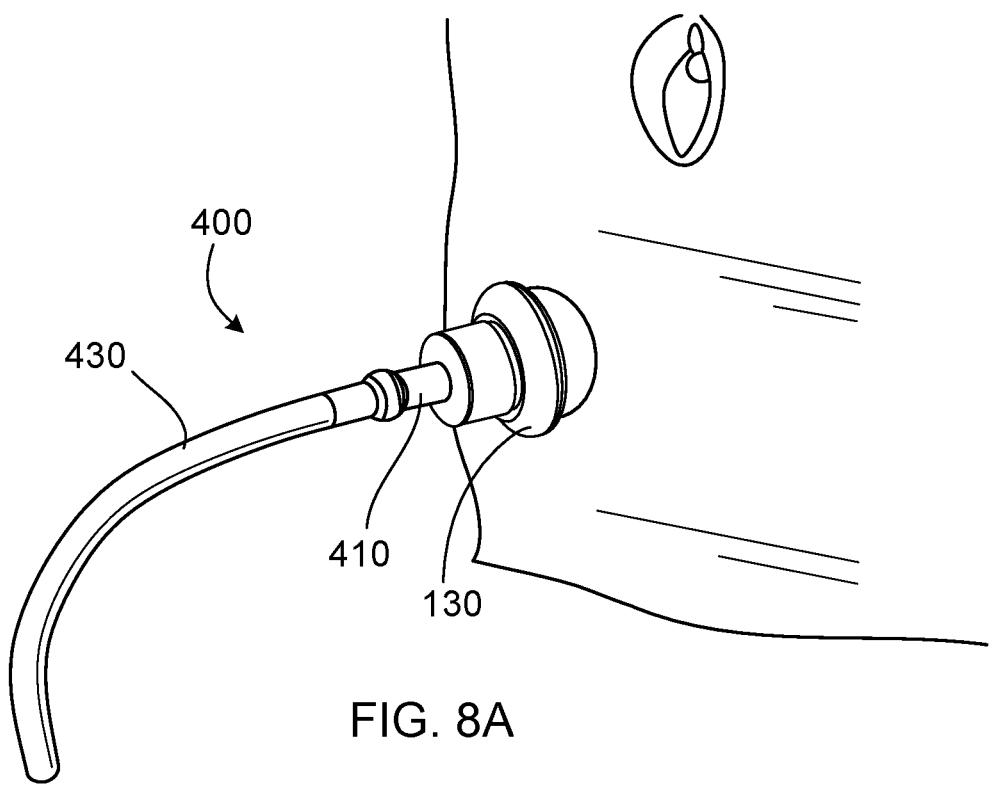
FIG. 8A is a perspective view of a drainage device as provided herein, where the drainage device is connected to drainage tubing and engaged with an embodiment of a valve device as provided herein, and where the valve device is positioned within a stoma.
Figure 8B:
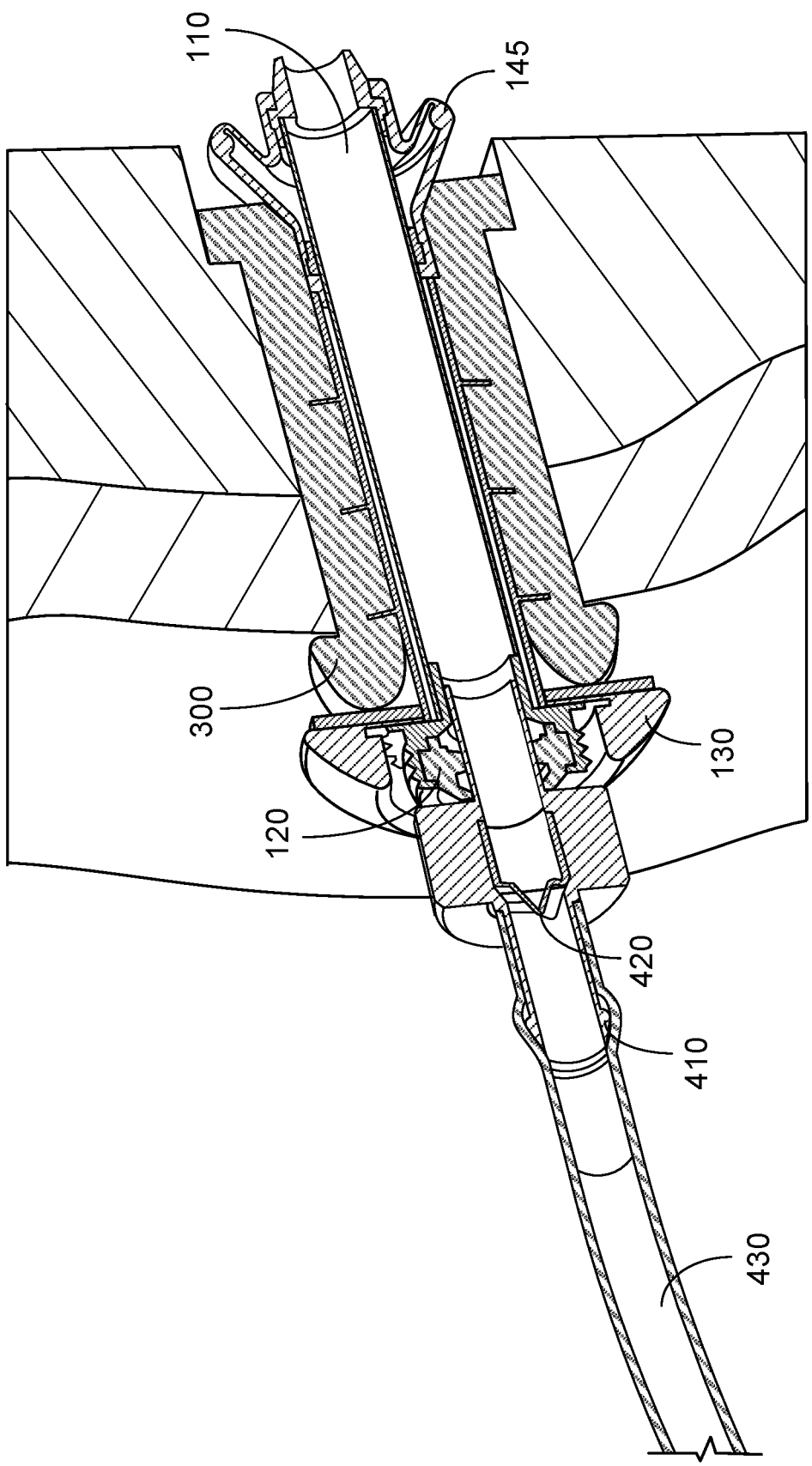
FIG. 8B is a cross-sectional view of a drainage device as provided herein, where the drainage device is connected to drainage tubing and engaged with an embodiment of a valve device as provided herein, and where the valve device is positioned within a stoma.

FIGS. 8A and 8B depict devices and a method for draining waste from a reservoir pouch. A drainage device 400 can include a relatively short, rigid segment of tubing 410, and a one way valve 420. The device 400 can be connected to a catheter or longer segment of tubing (e.g., the tubing 430) to facilitate drainage into a toilet, for example. The drainage device 400 can be inserted into the valve device 100 via the sealing element 120. The configuration and material of the sealing element 120 can allow the drainage device 400 to pass through the sealing element 120 without exterior leakage of waste, and also can allow the sealing element 120 to act as a wiper when the drainage device 400 is removed from the valve device 100. The one way valve 420 can prevent waste from flowing back out through the drainage device 400 when the drainage device 400 is removed from the valve device 100.

Figure 9A:
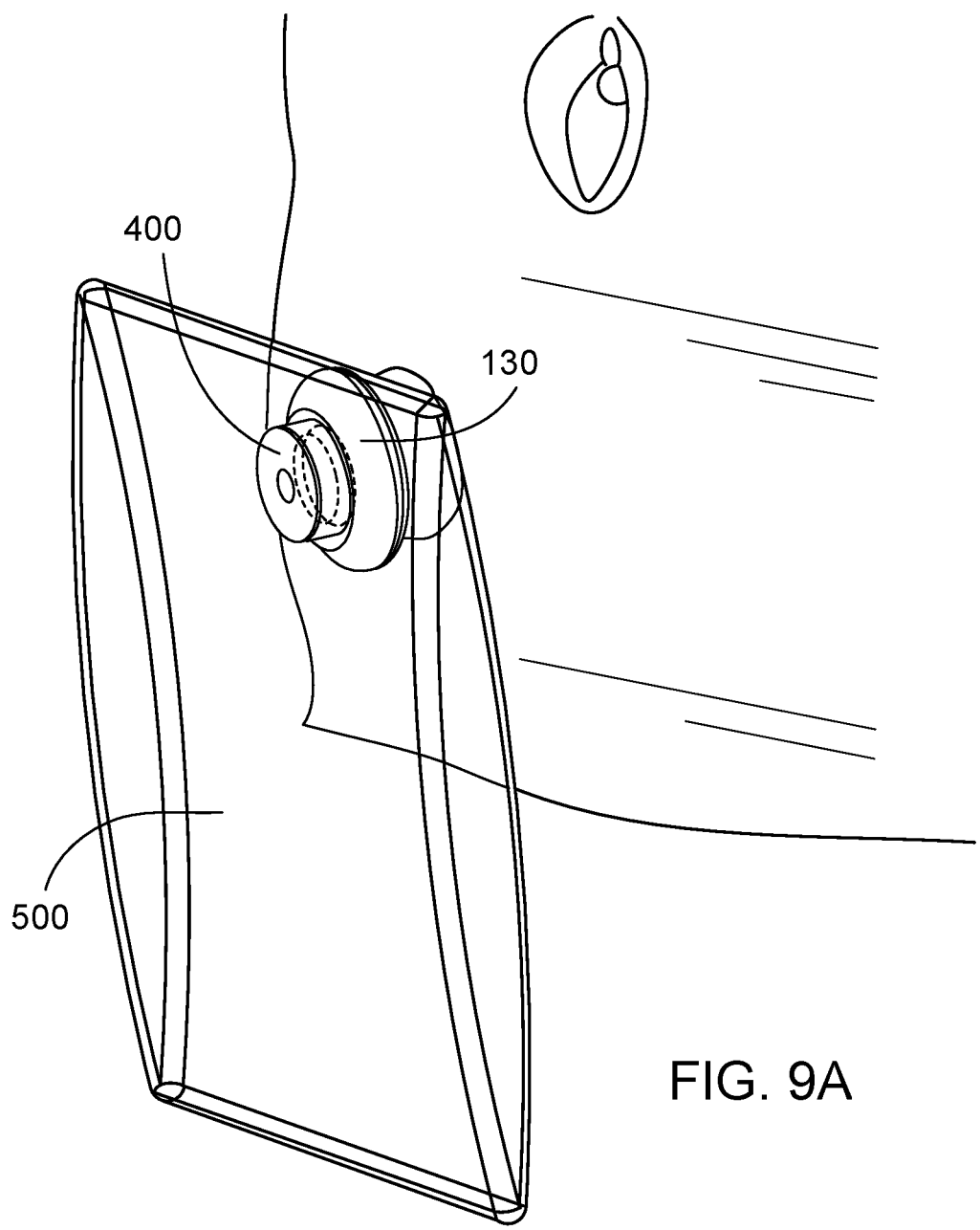
FIG. 9A is a perspective view of a drainage device as provided herein, where the drainage device is connected to a waste collection bag and engaged with an embodiment of a valve device as provided herein, and where the valve device is positioned within a stoma.
Figure 9B:
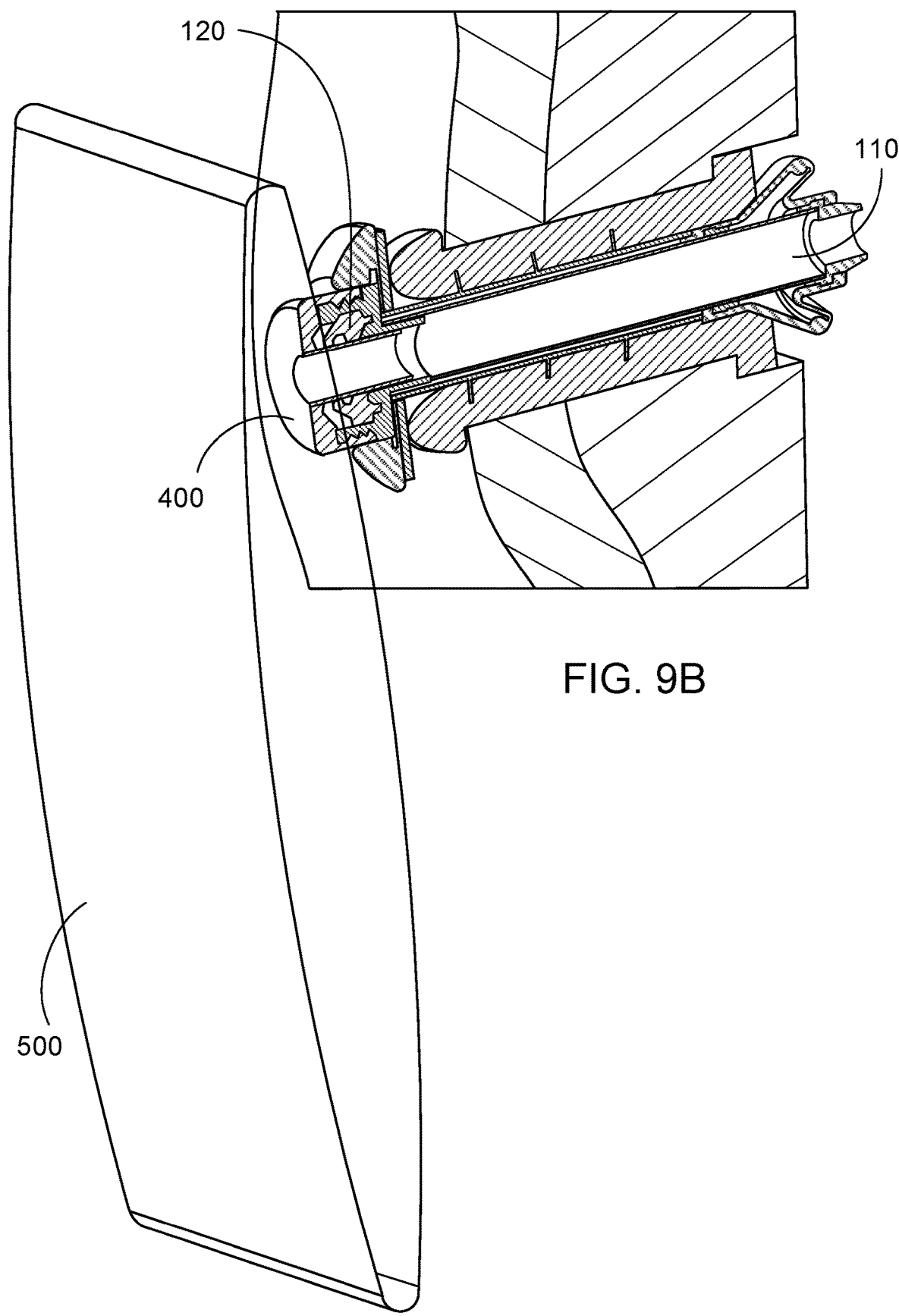
FIG. 9B is a cross-sectional view of a drainage device as provided herein, where the drainage device is connected to a waste collection bag and engaged with an embodiment of a valve device as provided herein, and where the valve device is positioned within a stoma.

In some embodiments, such as when longer periods of continence are desired by a user, a drainage bag can be connected to the valve device 100. As depicted in FIGS. 9A and 9B, for example, the drainage device 400 can be inserted into the valve device 100, but rather than connecting the drainage device 400 to a catheter or tubing, a drainage bag 500 can be connected to the drainage device 400. The drainage bag 500 can be made from any suitable material, including materials used to make ostomy bags that are standard in the art, for example. The drainage bag 500 can be disposable, or can be emptied and washed out. As described above, the one way valve 420 can prevent waste from flowing back out through the drainage device 400 when the drainage bag 500 and the device 400 are removed from the valve device 100. Any suitable means (e.g., clips, threaded head, sutures, tie downs, or adhesive) can be used for connecting the bag 500 to the drainage device 400.

Figure 10A:
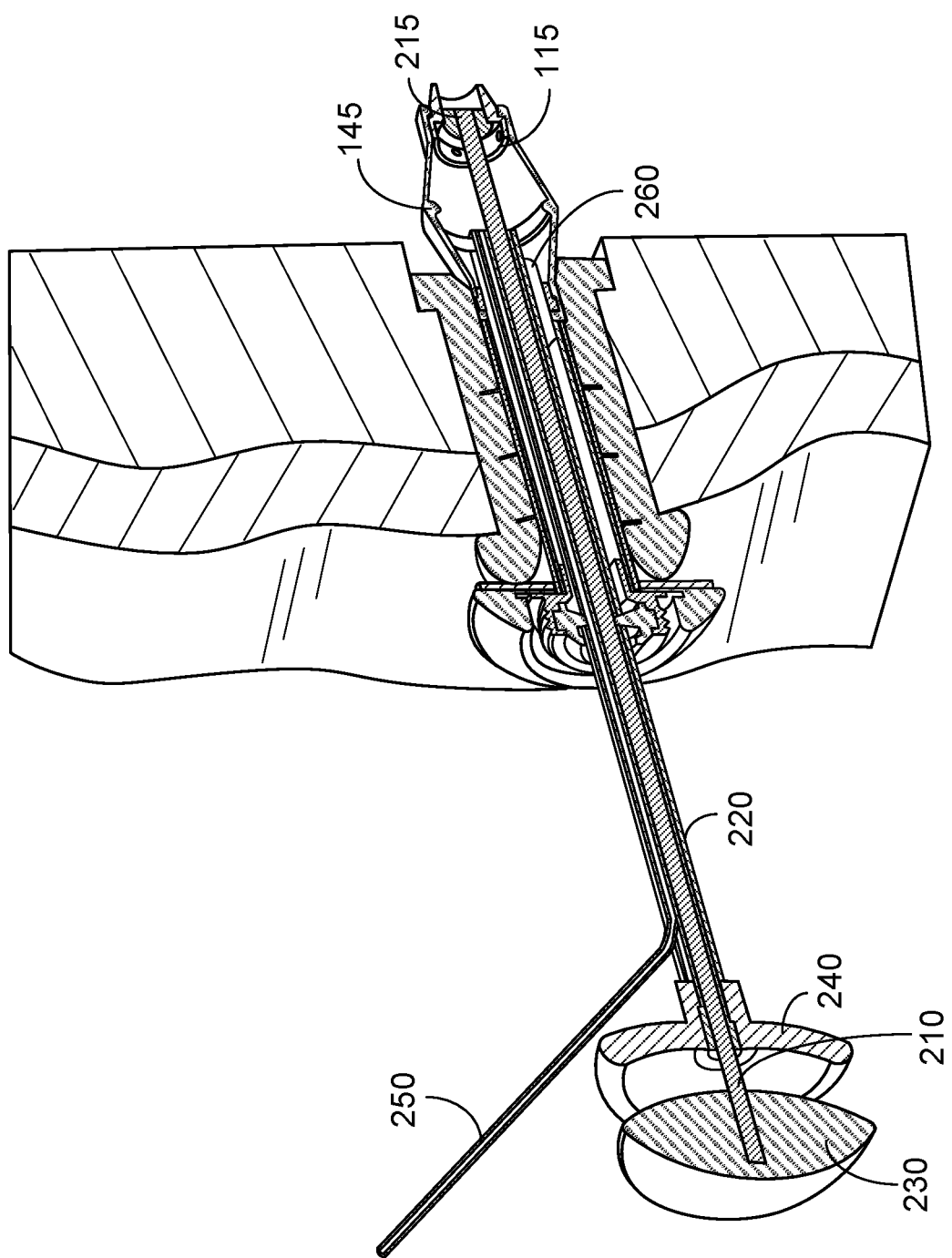
FIG. 10A is a cross-sectional view of an embodiment of an insertion/removal device as provided herein, engaged with an embodiment of a valve device as provided herein, with the valve device positioned within a stoma.
Figure 10B:
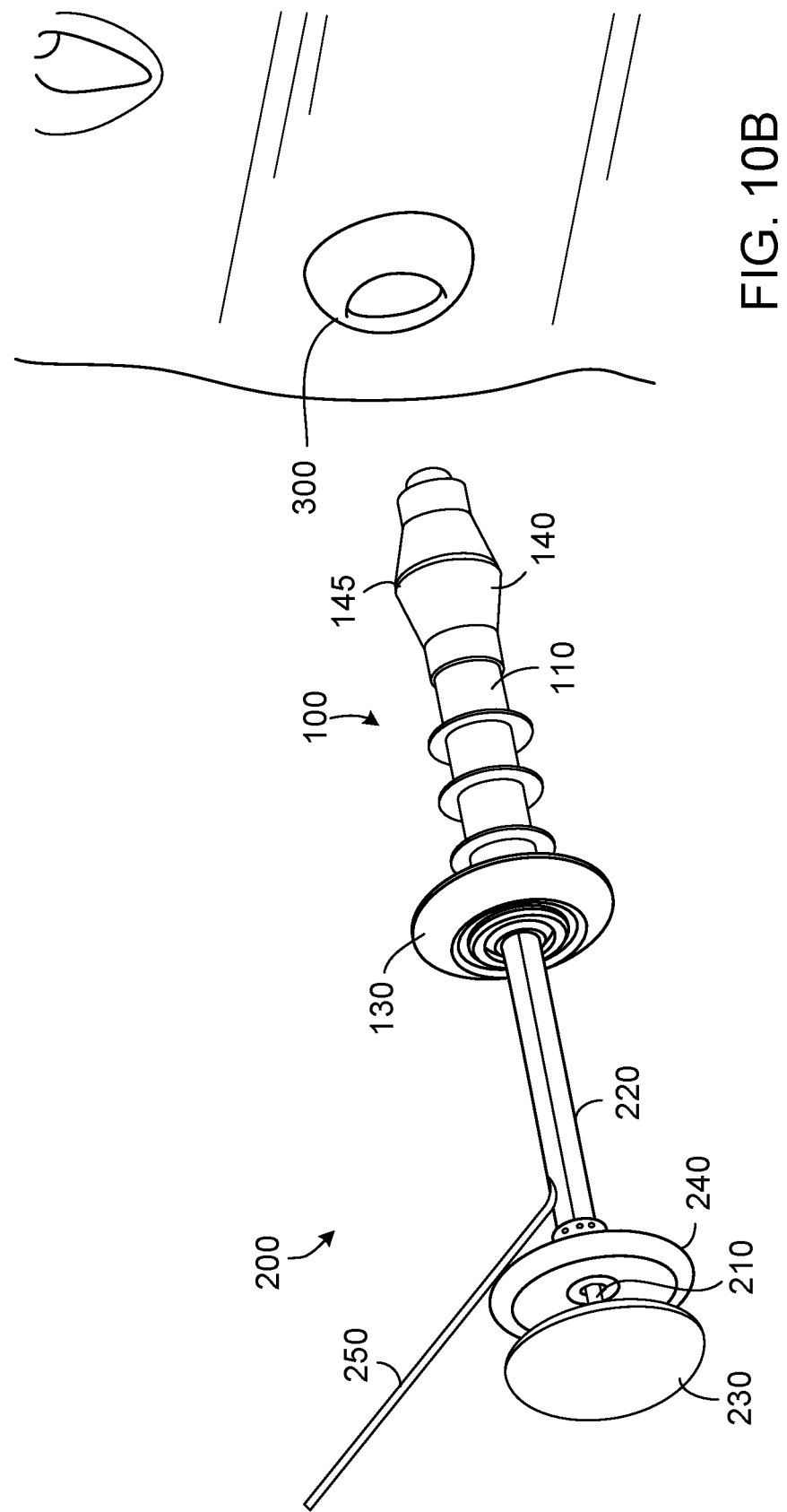
FIG. 10B is a perspective view of an embodiment of an insertion/removal device as provided herein, engaged with an embodiment of a valve device as provided herein, and positioned near a stoma.

FIGS. 10A and 10B depict the removal of the valve device 100 from the stoma 300 of a user. The procedure is essentially the reverse of that used to insert the valve device 100 into the stoma 300. The insertion/removal device 200 can be inserted into the valve device 100 via the sealing element 120, the paddle 215 can be engaged with the ridge 115, and the balloon 260 can be inflated via the port 250. Force exerted on the handles 230 and 240 by a user or clinician pushes the handle 230 closer to the handle 240 and/or pulls the handle 240 closer to the handle 230, such that the distal portion 214 of the inner shaft 210 is extended beyond the distal portion 224 of the hollow outer shaft 220. Due to the interaction between the paddle 215 and the ridge 115, the actuation of the handles 230 and 240 causes the valve device 100 to elongate, as shown in FIGS. 10A and 10B. The elongated, non-radially expanded valve device 100 then can be removed from the stoma 300 along with the insertion/removal device 200.

This document also provides articles of manufacture, or kits, that include one or more of the devices described herein. For example, an article of manufacture or kit can include one or more valve devices, one or more insertion/removal devices, one or more drainage devices, and combinations thereof, as well as packaging and instructions for using the devices. In some embodiments, an article of manufacture can include at least one valve device as described herein, and an insertion/removal device. Such embodiments also can include instructions for inserting and removing the valve device.

It is noted that the valve devices described herein can be of various sizes (e.g., lengths and diameters), to accommodate different users. In some embodiments, for example, a valve device can have a length along its tubular member, in a non-extended configuration, of about 2 cm to about 10 cm (e.g., about 2, 3, 4, 5, 6, 7, 8, 9, or 10 cm, or about 2 cm to about 5 cm, about 3 cm to about 6 cm, about 4 cm to about 7 cm, about 5 cm to about 8 cm, or about 6 cm to about 9 cm). When extended, the length of a valve device can be increased by at least about 0.5 cm to about 5 cm (e.g., about 0.5, 1, 1.5, 2, 2.5, 3, 3.5, 4, 4.5, or 5 cm, or about 0.5 cm to about 2 cm, about 1 cm to about 3 cm, or about 2 cm to about 4 cm). An insertion/removal device as provided herein can have a length that is compatible with a range of lengths of the valve devices described herein.

The valve devices provided herein also can be of different diameters. In some embodiments, for example, a valve device can have a tubular member with an exterior diameter (excluding fins and ribs, for example) of about 0.5 cm to about 3 cm (e.g., about 0.5, 1, 1.5, 2, 2.5, or 3 cm, or about 0.5 to about 1.5 cm, about 1 to about 2 cm, about 1.5 to about 2.5 cm, or about 2 to about 3 cm). The ribs, fins, or other structures on the external surface of the tubular member can extend beyond the external surface by about 0.3 cm to about 2 cm (e.g., about 0.3, 0.5, 0.7, 1, 1.2, 1.5, 1.7, or 2 cm, or about 0.3 to about 0.7, about 0.5 to about 1, about 1 to about 1.5, or about 1.5 to about 2 cm). In some embodiments, the interior diameter of the tubular member (the diameter of the lumen) can be about 0.3 cm to about 1 cm (e.g., about 0.3, 0.5, 0.7, 0.9, or 1 cm, or about 0.3 to about 0.6, about 0.4 to about 0.7, about 0.5 to about 0.8, about 0.6 to about 0.9, or about 0.7 to about 1 cm). Articles of manufacture can include valve devices of particular sizes, so that individual users can obtain devices that are appropriate for their own use.

It is noted that if a device as provided herein is to be used as an anal plug for fecal incontinence, a device length of about 4 cm to about 9 cm (e.g., about 4 cm to about 7 cm, about 5 cm to about 8 cm, or about 6 cm to about 9 cm) may be particularly useful. In such cases, particularly when a valve is to be used as an anal plug for a bed-ridden patient, the diameter of the valve may be larger than that disclosed above (e.g., about 4, about 5, or about 6 cm), to accommodate the evacuation of solid stool. Devices to be used as anal plugs in ambulatory subjects do not require such a large diameter, as the devices can be removed for evacuation and then replaced for continence. In addition, a valve for use as an anal plug may lack external ribs or fins, which can facilitate anchoring the device across the anal musculature.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for use with an ostomy valve, the device comprising:
   a hollow outer tube having a first end and a second end, wherein the first end is attached to a first handle;
   an inner shaft positioned axially and slidably within the hollow outer tube, wherein the inner shaft has a first end and a second end, wherein the first end is attached to a second handle, and wherein a portion of the inner shaft proximate to its first end passes through an opening in the first handle;
   an inflatable balloon positioned on an outer surface of the hollow outer tube distal to the first handle; and
   an inflation port in fluid communication with the inflatable balloon, wherein the inflation port extends from the inflatable balloon toward the first handle.

2. The device of claim 1, wherein force exerted on the first and second handles to bring the first and second handles closer together causes the second end of the inner shaft to extend beyond the second end of the hollow outer tube.

3. The device of claim 1, wherein the second end of the inner shaft defines a protrusion configured to engage a complementary feature on the inner surface of an ostomy valve that comprises:
   a hollow tubular member having a first end, a second end, an outer surface, an inner surface, and a lumen extending axially through the tubular member between the first and second ends;
   a sealing element contained within the lumen; and
   an anchoring element at or adjacent to the second end, wherein the ostomy valve is reversibly adjustable between a radially expanded configuration for retention in a stoma, and a non-radially expanded configuration for insertion into or removal from the stoma.

4. The device of claim 3, wherein when the protrusion is engaged with the complementary feature, force exerted on the first and second handles to bring the first and second handles closer together causes the second end of the inner shaft to extend beyond the second end of the hollow outer tube of the device, such that the ostomy valve is elongated into a non-radially expanded configuration.

5. The device of claim 1, wherein the inner shaft is longer than the hollow outer tube.

6. The device of claim 3, wherein the inflatable balloon, when inflated, is configured to hold the hollow outer tube of the device securely within the hollow tubular member of the ostomy valve.

7. The device of claim 3, wherein the complementary feature comprises a ridge.

8. The device of claim 4, wherein the ostomy valve in the non-radially expanded configuration is configured to be inserted into or removed from a stoma.

9. The device of claim 4, wherein when the protrusion is engaged with the complementary feature, force exerted on the first and second handles to bring the first and second handles away from each other causes the hollow tubular member of the ostomy valve to shorten and expand radially, such that the ostomy valve is securely retained in a stoma.

* * * * *